US011110085B2

(12) United States Patent
Zhou et al.

(10) Patent No.: US 11,110,085 B2
(45) Date of Patent: Sep. 7, 2021

(54) CO-SPRAY DRYING OF CIPROFLOXACIN AND COLISTIN AND THE USES THEREOF

(71) Applicant: Purdue Research Foundation, West Lafayette, IN (US)

(72) Inventors: Qi Zhou, West Lafayette, IN (US); Nivedita Shetty, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 16/395,302

(22) Filed: Apr. 26, 2019

(65) Prior Publication Data

US 2019/0328728 A1 Oct. 31, 2019

Related U.S. Application Data

(60) Provisional application No. 62/662,805, filed on Apr. 26, 2018.

(51) Int. Cl.

| | |
|---|---|
| ***A61K 9/16*** | (2006.01) |
| ***A61K 31/496*** | (2006.01) |
| ***A61K 9/00*** | (2006.01) |
| ***A61K 47/18*** | (2017.01) |
| ***A61K 38/12*** | (2006.01) |

(52) U.S. Cl.

CPC .......... *A61K 31/496* (2013.01); *A61K 9/0075* (2013.01); *A61K 38/12* (2013.01); *A61K 47/183* (2013.01)

(58) Field of Classification Search

CPC ...... A61K 9/16; A61K 47/552; A61K 9/1605; A61K 9/1611; A61K 9/1617; A61K 9/1682

See application file for complete search history.

(56) References Cited

U.S. PATENT DOCUMENTS

2015/0132386 A1* 5/2015 Heng ................. A61K 31/4375 424/489
2017/0209530 A1* 7/2017 Heng ................... A61K 31/407

OTHER PUBLICATIONS

Waterer, G., et al, "Respiratory infections: a current and future threat", Respirology. 2009, 14, 5, pp. 651-655.
Tran, T., et al, "Pharmacokinetics/pharmacodynamics of colistin and polymyxin B: are we there yet?", International journal of antimicrobial agents, 2016, 48, 6, pp. 592-597.
Zhou, Q., et al, "Colistin Powders with High Aerosolisation Efficiency for Respiratory Infection: Preparation and In Vitro Evaluation", Journal of Pharmaceutical Sciences, 2013, 102, 10, pp. 3736-3747.
Lin, Y., et al, "Pharmacokinetics/pharmacodynamics of pulmonary delivery of colistin against Pseudomonas aeruginosa in a mouse lung infection model", Antimicrobial agents and chemotherapy, 2017, 61, 3, pp. 11.
Buyck, J., et al, "Activities of antibiotic combinations against resistant strains of Pseudomonas aeruginosa in a model of infected THP-1 monocytes", Antimicrob Agents Chemother. 2015, 59, 1, pp. 258-268.
Pamp, S., et al, "Tolerance to the antimicrobial peptide colistin in Pseudomonas aeruginosa biofilms is linked to metabolically active cells, and depends on the pmr and mexAB-oprM genes", Molecular microbiology. 2008, 68, 1, pp. 223-240.
Lavorini, F., et al, "Recent advances in capsule-based dry powder inhaler technology", Multidiscip Respir Med. 2017, 12, 11, pp. 7.
Park, C., et al, "Advanced spray-dried design, physicochemical characterization, and aerosol dispersion performance of vancomycin and clarithromycin multifunctional controlled release particles for targeted respiratory delivery as dry powder inhalation aerosols", International journal of pharmaceutics, 2013, 455, 1-2, pp. 374-392.
Shetty, N., et al, "Effects of Moisture-Induced Crystallization on the Aerosol Performance of Spray Dried Amorphous Ciprofloxacin Powder Formulations", Pharm Res. 2018, 35, 1, 7, pp. 13.
Nie, H., et al, "Impact of metallic stearates on disproportionation of hydrochloride salts of weak bases in solid-state formulations", Molecular pharmaceutics, 2016, 13, 10, pp. 3541-3552.
Zhou, Q., et al, "Effect of device design on the aerosolization of a carrier-based dry powder inhaler—a case study on Aerolizer Foradile", The AAPS journal, 2013, 15, 2, pp. 511-522.
Zhou, Q.,et al, "How Much Surface Coating of Hydrophobic Azithromycin Is Sufficient to Prevent Moisture-Induced Decrease in Aerosolisation of Hygroscopic Amorphous Colistin Powder?", The AAPS journal, 2016, 18, 5, pp. 1213-1224.
Li, L, et al, "l-Leucine as an excipient against moisture on in vitro aerosolization performances of highly hygroscopic spray-dried powders", European Journal of Pharmaceutics and Biopharmaceutics, 2016, 102, pp. 132-141.
Zhou, Q, et al, "Synergistic antibiotic combination powders of colistin and rifampicin provide high aerosolization efficiency arid moisture protection", The AAPS journal, 2014, vol. 16, No. 1, pp. 37-47.
Mangal, S., et al, "Relationship between surface concentration of l-leucine and bulk powder properties in spray dried formulations", European Journal of Pharmaceutics and Biopharmaceutics, 2015, 94, pp. 160-169.
Mangal, S., et al, "Physico-Chemical Properties, Aerosolization and Dissolution of Co-Spray Dried Azithromycin Particles with L-Leucine for Inhalation", Pharmaceutical Research, 2018, 35, 28, pp. 15.

* cited by examiner

*Primary Examiner* — Micah Paul Young
(74) *Attorney, Agent, or Firm* — Purdue Research Foundation; Liang Zeng Yan

(57) ABSTRACT

The present disclosure generally relates to a combination dry powder inhaler (DPI) formulation of Ciprofloxacin and Colistin through co-spray drying, particularly to a co-sprayed colistin and Ciprofloxacin dry powder inhaler for the treatment of various bacterial infections. Methods of use and composition matters are within the scope of this disclosure.

19 Claims, 13 Drawing Sheets

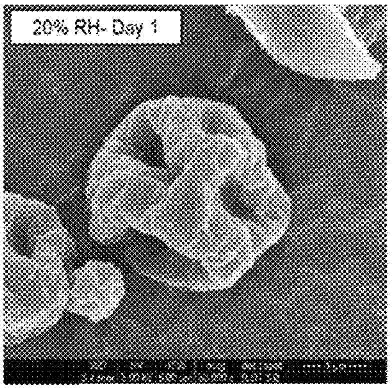
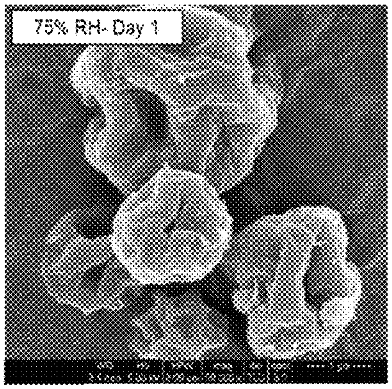
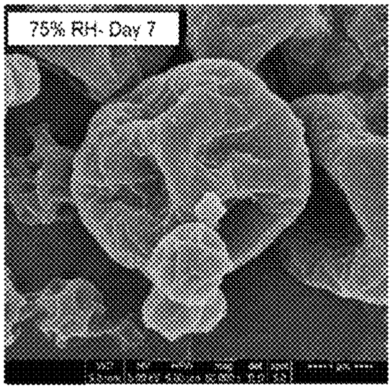
FIG. 14A FIG. 14B FIG. 14C
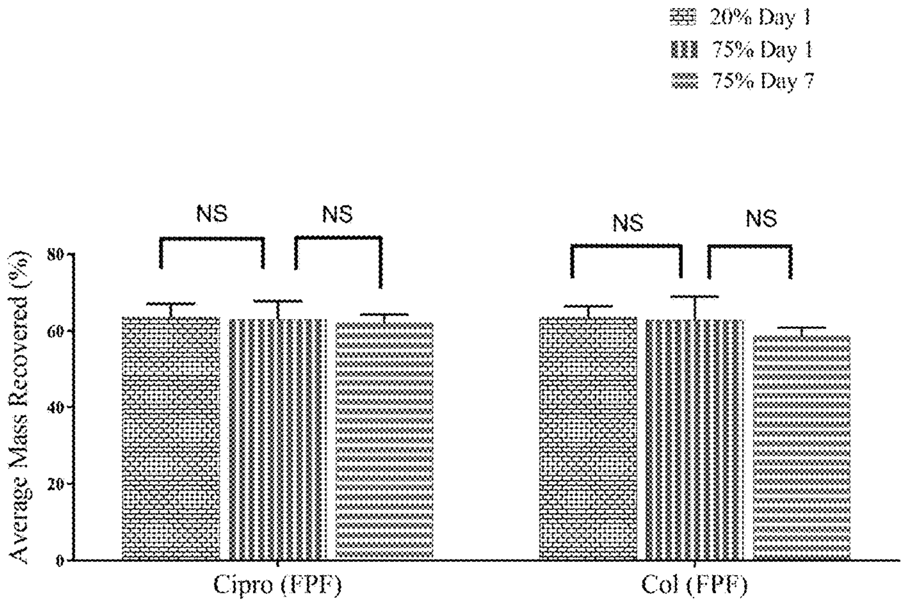
FIG. 15

CO-SPRAY DRYING OF CIPROFLOXACIN AND COLISTIN AND THE USES THEREOF

CROSS REFERENCE TO RELATED APPLICATIONS

This present patent application relates to and claims the priority benefit of U.S. Provisional Application Ser. No. 62/662,805, filed Apr. 26, 2018, the content of which is hereby incorporated herein by reference in its entirety.

GOVERNMENT SUPPORT CLAUSE

This invention was made with government support under AI132681 awarded by the National Institutes of Health. The government has certain rights in the invention.

TECHNICAL FIELD

The present application relates generally to a process for manufacturing a dry powder inhaler formulation, and specifically to co-spray drying of ciprofloxacin and colistin for the treatment of a bacterial infection.

BACKGROUND

This section introduces aspects that may help facilitate a better understanding of the disclosure. Accordingly, these statements are to be read in this light and are not to be understood as admissions about what is or is not prior art.

Lower respiratory infections (or lung infections) caused by Gram negative pathogens such as *Pseudomonas aeruginosa* are difficult to treat and were associated with high risks of mortality, morbidity and increased hospital stay (Waterer G., et al., *Respirology,* 2009, 14, 651-655). This is mainly due to the emergence of drug resistance against various first-line antimicrobials including Ciprofloxacin. Ciprofloxacin is one of the potent broad spectrum antibacterial considered as the preferred drug for respiratory tract infections including those caused by *Pseudomonas aeruginosa*. Due to its unique mode of action it was initially believed that the chances of development of drug resistance against Ciprofloxacin would be low. However, studies have shown that resistance development to Ciprofloxacin is rapid for some Gram negative bacteria (Kaatz G W, et al., *J. Infect. Dis.* 1988, 158, 537-541). High level of fluoroquinolone resistance appears to be due to alterations in the A subunit of DNA gyrase and in a simultaneous alteration in cell membrane permeability that probably is related to a loss of outer-membrane proteins. There are constant unmet needs for new treatment options to fight various ever changing bacterial infections.

SUMMARY

The present disclosure generally relates to a combination dry powder inhaler (DPI) formulation of Ciprofloxacin and Colistin through co-spray drying. Colistin in the formulation inhibited the tendency of amorphous Ciprofloxacin to crystallize when stored at 55% RH, resulting in enhanced physical stability. Such inhibition effect could be due to polymer-like properties of Colistin that acts as a matrix material and reduces the molecular mobility of Ciprofloxacin. Moreover, addition of Colistin improved the aerosolization as compared to the spray dried Ciprofloxacin alone formulation, which is attributed to enrichment of Colistin on the surface of the co-spray dried formulation as measured by XPS, EDX and Tof-SIMS. Further addition of L-leucine even prevented moisture-induced deterioration in aerosolization as stored at 75% RH. Our study for the first time demonstrated that co-spray drying Ciprofloxacin with a synergistic antibiotic Colistin not only enhances the physical stability of amorphous powder formulation but also improves the aerosolization through surface enrichment of Colistin. The in-vivo synergistic efficacy of such combination formulation will be examined using our established animal lung infections models.

In some illustrative embodiments, the present disclosure relates to a process for manufacturing a dry powder composition comprising the steps of a. dissolving a polymyxin compound and a quinolone compound, or a pharmaceutically acceptable salt thereof, respectively, in an aqueous or an organic medium to prepare a solution;
b. adding one or more pharmaceutically acceptable excipients to said solution; and
c. spray-drying of said solution.

In some illustrative embodiments, this present disclosure relates to a process for manufacturing a dry powder composition disclosed herein, wherein the process further comprises a step of adding an amino acid with a hydrophobic, aliphatic side chain to the solution of colistin and ciprofloxacin, wherein said amino acid with a hydrophobic, aliphatic side chain comprise leucine, isoleucine, valine and methionine.

In some preferred embodiments, this present disclosure relates to a process for manufacturing a dry powder composition disclosed herein, wherein said amino acid with a hydrophobic, aliphatic side chain is leucine.

In some illustrative embodiments, the present disclosure relates to a process for manufacturing a dry powder composition as disclosed herein, wherein said process further comprising a step of adding leucine to the solution of colistin and ciprofloxacin, wherein said leucine comprises about 10% to 60% of the total solid weight of the mixture of leucine/polymyxin/quinolone.

In some preferred embodiments, the present disclosure relates to a process for manufacturing a dry powder composition as disclosed herein, wherein said polymyxin is colistin or a pharmaceutically acceptable salt thereof, and said quinolone drug is ciprofloxancin or a pharmaceutically acceptable salt thereof.

In some illustrative embodiments, the present disclosure relates to a process for manufacturing a dry powder composition as disclosed herein, wherein said solution comprises about 5 to 200 mg of colistin and ciprofloxacin in a ratio of about 1:10 to about 10:1 (weight/weight) per milliliter.

In some illustrative embodiments, the present disclosure relates to a process for manufacturing a dry powder composition as disclosed herein, wherein said leucine comprises about 10% to 60% of the total solid weight of leucine/colistin/ciprofloxacin mixture.

In some illustrative embodiments, the present disclosure relates to a process for manufacturing a dry powder composition as disclosed herein, wherein the process further comprising a step of adding leucine to the solution of colistin and ciprofloxacin, wherein said leucine comprises about 10% to 60% of the total solid weight of the mixture of leucine/colistin/ciprofloxacin.

In some illustrative embodiments, the present disclosure relates to a process for manufacturing a dry powder composition as disclosed herein, wherein said mixture of leucine/colistin/ciprofloxacin were in a ratio of about 1:1:1 (weight/weight).

In some illustrative embodiments, the present disclosure relates to a process for manufacturing a dry powder composition as disclosed herein, wherein said solution comprises about 5 to 200 mg of colistin and ciprofloxacin in a ratio of about 1:10 to about 10:1 (weight/weight) per milliliter.

In some illustrative embodiments, the present disclosure relates to a process for manufacturing a dry powder composition as disclosed herein, wherein said aqueous medium is water or an aqueous solution of an organic solvent selected from the group consisting of acetonitrile, methanol, ethanol, or isopropyl alcohol wherein said organic solvent is to improve the solubility of drug material colistin/ciprofloxacin which could not be fully dissolved in pure water.

In some illustrative embodiments, the present disclosure relates to a dry powder composition manufactured according to the process disclosed herein.

In some illustrative embodiments, the present disclosure relates to a dry powder composition manufactured according to the process disclosed herein, wherein leucine, colistin and ciprofloxacin are in a ratio of about 1:1:1 (weight/weight).

In some illustrative embodiments, the present disclosure relates to a pharmaceutical composition comprising a product manufactured according to the process disclosed herein together with one or more pharmaceutically acceptable excipients.

In some other illustrative embodiments, the present disclosure relates to a pharmaceutical composition comprising a product manufactured according to a pharmaceutical composition manufactured according to a process comprising the steps of:

a. dissolving colistin and ciprofloxacin in an aqueous medium to prepare a solution;
b. adding one or more pharmaceutically acceptable excipients to said solution; and
c. spray-drying of said solution.

In some other illustrative embodiments, the present disclosure relates to a pharmaceutical composition manufactured according to a process disclosed herein, wherein said process further comprising a step of adding leucine to the solution of colistin and ciprofloxacin, wherein said leucine comprises about 10% to 60% of the total solid weight of the mixture of leucine/colistin/ciprofloxacin.

In some illustrative embodiments, the present disclosure relates to a pharmaceutical composition comprising a product manufactured according to the process disclosed herein together with one or more pharmaceutically acceptable excipients, wherein said solution comprises about 5 to 200 mg of colistin and ciprofloxacin per milliliter.

In some illustrative embodiments, the present disclosure relates to a pharmaceutical composition comprising a product manufactured according to the process disclosed herein together with one or more pharmaceutically acceptable excipients, wherein colistin and ciprofloxacin are in a ratio of about 1:10 to about 10:1 (weight/weight).

In some illustrative embodiments, the present disclosure relates to a pharmaceutical composition comprising a product manufactured according to the process disclosed herein together with one or more pharmaceutically acceptable excipients, wherein said pharmaceutical composition is administered by inhalation.

In some illustrative embodiments, the present disclosure relates to a method for treating a patient with a bacterial infection comprising the step of administering a therapeutically effective amount of a pharmaceutical composition to a patient in need of relief from said infection, wherein said pharmaceutical composition is manufactured according to a process comprising the steps of a. dissolving colistin and ciprofloxacin in an aqueous medium to prepare a solution;
b. adding one or more pharmaceutically acceptable excipients to said solution; and
c. spray-drying of said solution.

In some illustrative embodiments, the present disclosure relates to a method for treating a patient with a bacterial infection comprising the step of administering a therapeutically effective amount of a pharmaceutical composition to a patient in need of relief from said infection, wherein said process further comprising a step of adding leucine to the solution of colistin and ciprofloxacin, wherein said leucine comprises about 10% to 60% of the total solid weight of leucine/colistin/ciprofloxacin mixture.

In some illustrative embodiments, the present disclosure relates to a method for treating a patient with a bacterial infection comprising the step of administering a therapeutically effective amount of a pharmaceutical composition to a patient in need of relief from said infection, wherein said infection is an infection of the lungs.

In some illustrative embodiments, the present disclosure relates to a method for treating a patient with a bacterial infection comprising the step of administering a therapeutically effective amount of a pharmaceutical composition to a patient in need of relief from said infection, wherein said infection is an infection caused by *Pseudomonas aeruginosa, Acinetobacter baumannii* and *Klebsiella pneumoniae.*

In some illustrative embodiments, the present disclosure relates to a method for treating a patient with a bacterial infection comprising the step of administering a therapeutically effective amount of a pharmaceutical composition to a patient in need of relief from said infection, wherein said pharmaceutical composition is administered by inhalation.

These and other features, aspects and advantages of the present invention will become better understood with reference to the following figures, descriptions and claims.

BRIEF DESCRIPTION OF THE DRAWINGS

The above and other objects, features, and advantages of the present invention will become more apparent when taken in conjunction with the following description and drawings wherein identical reference numerals have been used, where possible, to designate identical features that are common to the figures, and wherein:

FIG. 1A immediately after spray drying; FIG. 1B stored at 20% Relative Humidity (RH) after 60 days; FIG. 1C stored at 55% RH after 1 day; FIG. 1D stored at 55% RH after 3 days; and FIG. 1E stored at 55% RH after 60 days.

FIG. 4A, Raw Ciprofloxacin; FIG. 4B, Raw Colistin; FIG. 4C, Colistin-Ciprofloxacin (1:9); FIG. 4D, Colistin-Ciprofloxacin (1:3); and FIG. 4E, Colistin: Ciprofloxacin (1:1) (scale bar represents 10 μm).

FIGS. 6A-6E depict moisture sorption isotherms for: FIG. 6A, Spray-Dried (SD) Ciprofloxacin (Cipro) alone; FIG. 6B, SD Colistin (Col) alone; FIG. 6C, SD Col/Cipro (1:9); FIG. 6D, SD Col/Cipro (1:3); and FIG. 6E, SD Col/Cipro (1:1).

FIG. 7A, ColCip (1:9); FIG. 7B, ColCip (1:3); and FIG. 7C, ColCip (1:1) which were stored at 20% relative humidity (RH) and 55% RH (mean±SD, n=4; NS, no significant difference)

FIG. 14A demonstrates SEM micrographs for the co-spray dried Colistin-Ciprofloxacin-leucine formulation in the mass ratio (1:1:1) stored at 20% RH at Day 1. FIG. 14B depicts SEM micrographs for the co-spray dried Colistin-Ciprofloxacin-leucine formulation in the mass ratio (1:1:1) stored at 75% RH at Day 1. FIG. 14C depicts SEM micrographs for the co-spray dried Colistin-Ciprofloxacin-leucine formulation in the mass ratio (1:1:1) stored at 75% RH at Day 7.

FIG. 15 shows In-vitro aerosol performance of Ciprofloxacin and Colistin in the co-spray dried ColCipLeu formulation with mass ratios (1:1:1) stored at 75% RH for 7 days (mean±SD, n=4; NS, no significant difference).

DETAILED DESCRIPTION

Figure 1A:
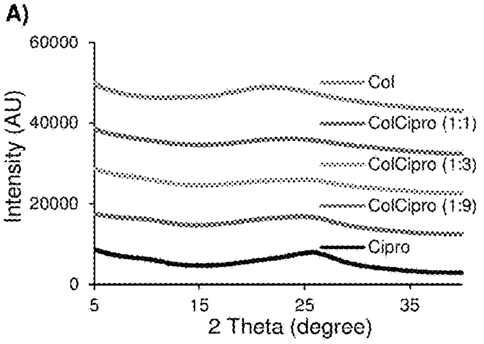
FIGS. 1A-1E show X-ray diffraction patterns of the drug alone and co-spray dried powder formulations.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

In some illustrative embodiments, the present disclosure relates to a process for manufacturing a dry powder composition comprising the steps of a. dissolving a polymyxin compound and a quinolone compound, or a pharmaceutically acceptable salt thereof, respectively, in an aqueous or an organic medium to prepare a solution;
b. adding one or more pharmaceutically acceptable excipients to said solution; and
c. spray-drying of said solution.

In some illustrative embodiments, this present disclosure relates to a process for manufacturing a dry powder composition disclosed herein, wherein the process further comprises a step of adding an amino acid with a hydrophobic, aliphatic side chain to the solution of colistin and ciprofloxacin, wherein said amino acid with a hydrophobic, aliphatic side chain comprise leucine, isoleucine, valine and methionine.

In some preferred embodiments, this present disclosure relates to a process for manufacturing a dry powder composition disclosed herein, wherein said amino acid with a hydrophobic, aliphatic side chain is leucine.

In some illustrative embodiments, the present disclosure relates to a process for manufacturing a dry powder composition as disclosed herein, wherein said process further comprising a step of adding leucine to the solution of colistin and ciprofloxacin, wherein said leucine comprises about 10% to 60% of the total solid weight of the mixture of leucine/polymyxin/quinolone.

In some preferred embodiments, the present disclosure relates to a process for manufacturing a dry powder composition as disclosed herein, wherein said polymyxin is colistin or a pharmaceutically acceptable salt thereof, and said quinolone drug is ciprofloxancin or a pharmaceutically acceptable salt thereof.

In some illustrative embodiments, this present disclosure relates to a process for manufacturing a dry powder composition comprising the steps of a. dissolving colistin and ciprofloxacin in an aqueous or organic medium to prepare a solution;
b. adding one or more pharmaceutically acceptable excipients; and
c. spray-drying of said solution.

In some illustrative embodiments, this present disclosure relates to a process for manufacturing a dry powder composition, wherein said solution comprises colistin and ciprofloxacin in a ratio of about 1:10 to about 10:1 (weight/weight).

In some illustrative embodiments, this present disclosure relates to a process for manufacturing a dry powder composition, wherein said solution comprises about 5 to 200 mg of colistin and ciprofloxacin in a ratio of about 1:10 to about 10:1 (weight/weight) per milliliter.

In some illustrative embodiments, this present disclosure relates to a process for manufacturing a dry powder composition, wherein said aqueous medium is water or an aqueous solution of an organic solvent selected from the group consisting of acetonitrile, methanol, ethanol, or isopropyl alcohol wherein said organic solvent is to improve the solubility of the solid drug materials which could not be fully dissolved in pure water.

In some illustrative embodiments, this present disclosure relates to a process for manufacturing a dry powder composition disclosed herein, wherein the process further comprises a step of adding an amino acid with a hydrophobic, aliphatic side chain to the solution of colistin and ciprofloxacin, wherein said amino acid with a hydrophobic, aliphatic side chain comprise leucine, isoleucine, valine and methionine.

In some illustrative embodiments, this present disclosure relates to a process for manufacturing a dry powder composition disclosed herein, wherein said amino acid with a hydrophobic, aliphatic side chain is leucine.

In some illustrative embodiments, this present disclosure relates to a process for manufacturing a dry powder composition, wherein said leucine comprises about 10% to 60% of the total solid weight of leucine/colistin/ciprofloxacin mixture.

In some illustrative embodiments, this present disclosure relates to a process for manufacturing a dry powder composition, wherein said mixture of leucine/colistin/ciprofloxacin were in a ratio of about 1:1:1 (weight/weight).

In some illustrative embodiments, this present disclosure relates to a dry powder composition manufactured according to the process disclosed herein.

In some illustrative embodiments, this present disclosure relates to a dry powder composition manufactured according to the process disclosed herein, wherein leucine, colistin and ciprofloxacin are in a ratio of about 1:1:1 (weight/weight).

In some illustrative embodiments, this present disclosure relates to a dry powder composition manufactured according to the process disclosed herein, wherein colistin and ciprofloxacin are in a ratio of about 1:10 to about 10:1.

In some illustrative embodiments, this present disclosure relates to a dry powder composition manufactured according to the process disclosed herein, wherein colistin and ciprofloxacin are in a ratio of about 1:3 to about 3:1.

In some illustrative embodiments, this present disclosure relates to a pharmaceutical composition comprising the product manufactured according to the process disclosed herein together with one or more pharmaceutically acceptable excipients.

In some illustrative embodiments, this present disclosure relates to a pharmaceutical composition manufactured according to the process of:

a. dissolving colistin and ciprofloxacin in an aqueous or organic medium to prepare a solution;
b. adding one or more pharmaceutically acceptable excipients; and
c. spray-drying of said solution.

In some illustrative embodiments, this present disclosure relates to a pharmaceutical composition manufactured according to the process disclosed herein, wherein said solution comprises about 5 to 200 mg of colistin and ciprofloxacin per milliliter.

In some illustrative embodiments, this present disclosure relates to a pharmaceutical composition manufactured according to the process disclosed herein, wherein colistin and ciprofloxacin are in a ratio of about 1:10 to about 10:1 (weight/weight)

In some illustrative embodiments, this present disclosure relates to a pharmaceutical composition manufactured according to the process disclosed herein, wherein said pharmaceutical composition is administered by inhalation.

In some illustrative embodiments, this present disclosure relates to a method for treating a patient with a bacterial infection comprising the step of administering a therapeutically effective amount of the pharmaceutical composition disclosed herein, to a patient in need of relief from said infection.

In some illustrative embodiments, this present disclosure relates to a method for treating a patient with a bacterial infection comprising the step of administering a therapeutically effective amount of the pharmaceutical composition disclosed herein, to a patient in need of relief from said infection, wherein said infection is an infection of the lungs.

In some illustrative embodiments, this present disclosure relates to a method for treating a patient with a bacterial infection comprising the step of administering a therapeutically effective amount of the pharmaceutical composition disclosed herein, to a patient in need of relief from said infection, wherein said infection is caused by *Pseudomonas aeruginosa, Acinetobacter baumannii* and *Klebsiella pneumoniae.*

In some illustrative embodiments, this present disclosure relates to a method for treating a patient with a bacterial infection comprising the step of administering a therapeutically effective amount of the pharmaceutical composition disclosed herein, to a patient in need of relief from said infection, wherein said pharmaceutical composition is administered by inhalation.

In some illustrative embodiments, this present disclosure relates to a method for treating a patient with a bacterial infection comprising the step of administering a therapeutically effective amount of the dry powder composition disclosed herein, together with optional one or more carriers, diluents, or excipients, to a patient in need of relief from said infection.

In some illustrative embodiments, this present disclosure relates to a method for treating a patient with a bacterial infection comprising the step of administering a therapeutically effective amount of the dry powder composition disclosed herein, to a patient in need of relief from said infection, wherein said infection is an infection of the lungs.

In some illustrative embodiments, this present disclosure relates to a method for treating a patient with a bacterial infection comprising the step of administering a therapeutically effective amount of the dry powder composition disclosed herein, to a patient in need of relief from said infection, wherein said infection is caused by *Pseudomonas aeruginosa, Acinetobacter baumannii* and *Klebsiella pneumoniae.*

In some illustrative embodiments, this present disclosure relates to a method for treating a patient with a bacterial infection comprising the step of administering a therapeutically effective amount of the dry powder composition disclosed herein, to a patient in need of relief from said infection, wherein said dry powder composition is administered by inhalation.

As used herein, the following terms and phrases shall have the meanings set forth below.

Unless defined otherwise, all technical and scientific terms used herein have the same meaning as commonly understood to one of ordinary skill in the art.

In the present disclosure the term "about" can allow for a degree of variability in a value or range, for example, within 20%, within 10%, within 5%, or within 1% of a stated value or of a stated limit of a range.

In the present disclosure the term "substantially" can allow for a degree of variability in a value or range, for example, within 80%, within 90%, within 95%, or within 99% of a stated value or of a stated limit of a range.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting. Further, information that is relevant to a section heading may occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

As used herein, the term "salts" and "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. Pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

Pharmaceutically acceptable salts can be synthesized from the parent compound which contains a basic or acidic moiety by conventional chemical methods. In some instances, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, the disclosure of which is hereby incorporated by reference.

The term "solvate" means a compound, or a salt thereof, that further includes a stoichiometric or non-stoichiometric amount of solvent bound by non-covalent intermolecular forces. Where the solvent is water, the solvate is a hydrate.

The term "prodrug" means a derivative of a compound that can hydrolyze, oxidize, or otherwise react under biological conditions (in vitro or in vivo) to provide an active compound, particularly a compound of the invention. Examples of prodrugs include, but are not limited to, derivatives and metabolites of a compound of the invention that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Specific prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger's Medicinal Chemistry and Drug Discovery 6th ed. (Donald J. Abraham ed., 2001, Wiley) and Design and Application of Prodrugs (H. Bundgaard ed., 1985, Harwood Academic Publishers GmbH).

Further, in each of the foregoing and following embodiments, it is to be understood that the formulae include and represent not only all pharmaceutically acceptable salts of the compounds, but also include any and all hydrates and/or solvates of the compound formulae or salts thereof. It is to be appreciated that certain functional groups, such as the hydroxy, amino, and like groups form complexes and/or coordination compounds with water and/or various solvents, in the various physical forms of the compounds. Accordingly, the above formulae are to be understood to include and represent those various hydrates and/or solvates. In each of the foregoing and following embodiments, it is also to be understood that the formulae include and represent each possible isomer, such as stereoisomers and geometric isomers, both individually and in any and all possible mixtures. In each of the foregoing and following embodiments, it is also to be understood that the formulae include and represent any and all crystalline forms, partially crystalline forms, and non-crystalline and/or amorphous forms of the compounds.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As used herein, the term "administering" includes all means of introducing the compounds and compositions described herein to the patient, including, but are not limited to, oral (po), intravenous (iv), intramuscular (im), subcutaneous (sc), transdermal, inhalation, buccal, ocular, sublingual, vaginal, rectal, and the like. The compounds and compositions described herein may be administered in unit dosage forms and/or formulations containing conventional nontoxic pharmaceutically acceptable carriers, adjuvants, and vehicles.

Illustrative formats for oral administration include tablets, capsules, elixirs, syrups, and the like. Illustrative routes for parenteral administration include intravenous, intraarterial, intraperitoneal, epidural, intraurethral, intrasternal, intramuscular and subcutaneous, as well as any other art recognized route of parenteral administration.

Illustrative means of parenteral administration include needle (including microneedle) injectors, needle-free injectors and infusion techniques, as well as any other means of parenteral administration recognized in the art. Parenteral formulations are typically aqueous solutions which may contain excipients such as salts, carbohydrates (lactose, mannitol, sucrose, trehalose) and buffering agents (preferably at a pH in the range from about 3 to about 9), but, for some applications, they may be more suitably formulated as a sterile nonaqueous solution or as a dried form to be used in conjunction with a suitable vehicle such as sterile, pyrogen-free water. The preparation of parenteral formulations under sterile conditions, for example, by lyophilization, may readily be accomplished using standard pharmaceutical techniques well known to those skilled in the art. Parenteral administration of a compound is illustratively performed in the form of saline solutions or with the compound incorporated into liposomes. In cases where the compound in itself is not sufficiently soluble to be dissolved, a solubilizer such as ethanol can be applied.

The dosage of each compound of the claimed combinations depends on several factors, including: the administration method, the condition to be treated, the severity of the condition, whether the condition is to be treated or prevented, and the age, weight, and health of the person to be treated. Additionally, pharmacogenomic (the effect of genotype on the pharmacokinetic, pharmacodynamic or efficacy profile of a therapeutic) information about a particular patient may affect the dosage used.

It is to be understood that in the methods described herein, the individual components of a co-administration, or combination can be administered by any suitable means, contemporaneously, simultaneously, sequentially, separately or in a single pharmaceutical formulation. Where the co-administered compounds or compositions are administered in separate dosage forms, the number of dosages administered per day for each compound may be the same or different. The compounds or compositions may be administered via the same or different routes of administration. The compounds or compositions may be administered according to simultaneous or alternating regimens, at the same or different times during the course of the therapy, concurrently in divided or single forms.

The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician of ordinary skill.

Depending upon the route of administration, a wide range of permissible dosages are contemplated herein, including doses falling in the range from about 1 μg/kg to about 1 g/kg. The dosages may be single or divided, and may administered according to a wide variety of protocols, including q.d. (once a day), b.i.d. (twice a day), t.i.d. (three times a day), or even every other day, once a week, once a month, once a quarter, and the like. In each of these cases it is understood that the therapeutically effective amounts described herein correspond to the instance of administration, or alternatively to the total daily, weekly, month, or quarterly dose, as determined by the dosing protocol.

In addition to the illustrative dosages and dosing protocols described herein, it is to be understood that an effective amount of any one or a mixture of the compounds described herein can be determined by the attending diagnostician or physician by the use of known techniques and/or by observing results obtained under analogous circumstances. In determining the effective amount or dose, a number of factors are considered by the attending diagnostician or physician, including, but not limited to the species of mammal, including human, its size, age, and general health, the specific disease or disorder involved, the degree of or involvement or the severity of the disease or disorder, the response of the individual patient, the particular compound administered, the mode of administration, the bioavailability characteristics of the preparation administered, the dose regimen selected, the use of concomitant medication, and other relevant circumstances.

The term "patient" includes human and non-human animals such as companion animals (dogs and cats and the like) and livestock animals. Livestock animals are animals raised for food production. The patient to be treated is preferably a mammal, in particular a human being.

Spray drying is a method of producing a dry powder from a liquid or slurry by rapidly drying with a hot gas. This is the preferred method of drying of many thermally-sensitive materials such as foods and pharmaceuticals. Air is the heated drying medium; however, if the liquid is a flammable solvent such as ethanol or the product is oxygen-sensitive then nitrogen is used.

Combining Ciprofloxacin with another antibiotic could be a good choice for controlling drug resistance against Ciprofloxacin. Combination of Ciprofloxacin with polypeptide antibiotic like Colistin, maximized therapeutic efficacy and minimized resistance development, in severe lung infections caused by Gram negative pathogens (Tran T B, et al., *Int. J. Antimicrobial Agents* 2016, 48, 592-597).

Polymyxins are peptide antibiotics, such as polymyxins B and E (also known as colistin), widely used in the treatment of Gram-negative bacterial infections. They work mostly by breaking up the bacterial cell membrane. They are part of a broader class of molecules called nonribosomal peptides. A quinolone antibiotic is a member of a large group of broad-spectrum bactericides that share a bicyclic core structure of 4-quinolone. They are used in human and veterinary medicine to treat bacterial infections, as well as in animal husbandry. Nearly all quinolone antibiotics are fluoroquinolones, which contain a fluorine atom in their chemical structure and are effective against both Gram-negative and Gram-positive bacteria. One example is ciprofloxacin, one of the most widely used antibiotics worldwide. Other quinolone drugs include Levofloxacin, Moxifloxacin, Gemifloxacin, Gatifloxacin, Garenoxacin.

Colistin, despite being an old antibiotic has retained its excellent antibacterial activity against Gram negative bacteria including *Pseudomonas* species (Zhou Q, et al., *J. Pharm. Sci.* 2013, 102, 3736-3747). The only limitation being nephrotoxicity at higher systemic concentrations. However, inhaled Colistin has shown to be safe and well tolerated in patients with chronic *Pseudomonas aeruginosa* infection and also based on PK/PD data from animal and clinical studies inhaled Colistin has shown in-vivo advantage over systemic administration (Haworth C S, et al, *Am J. Respir. Critical Care Med.* 2014, 189, 975-982; Lin, Y W, et al., *Antimicro. Agents Chemother.* 2017, 61, e02025-02016).

Prentice et al. compared the various combinations of antibiotics to study their ability to prevent emergence of resistance in Gram negative pathogens and they found that the combination of oral Ciprofloxacin with Colistin could successfully prevent emergence of resistance even when used continuously for 10 years as a prophylactic regimen (Prentice H G et al., *Brit. J. Haematol.* 2001, 115, 46-52). While the exact mechanism of the synergistic action of Ciprofloxacin with Colistin remains uncertain, Colistin seems to enhance uptake of the companion antibiotic through its destabilizing effects on the outer membrane of the bacteria. Combination of Ciprofloxacin with Colistin was also found to be useful in 'difficult to tackle' *Pseudomonas aeruginosa* biofilms; the ability to form biofilm by *Pseudomonas aeruginosa* is associated with severe respiratory infections. Ciprofloxacin effectively eliminates metabolically active pathogenic population of the biofilm while Colistin specifically kills the bacterial population with low metabolic activity (Pamp S J, et al., *Mol. Microbiol.* 2008, 68, 223-240). The biofilm cells can thus be totally eliminated by using two antibacterial drugs, Colistin and Ciprofloxacin, each with a specific activity on a physiological subpopulation.

Use of antibiotics in the inhalation form is another important development which has contributed to better control of severe lower respiratory infections. A combination of nebulized Colistimethane sodium and oral Ciprofloxacin have been successfully used in eradicating multidrug resistant *Pseudomonas aeruginosa* associated with severe lower respiratory infections (Li J. et al., *Lancet Infect. Dis.* 2006, 6, 589-601). But nebulizers used in inhalation therapy including the commonly used jet nebulizers have certain disadvantages such as—need for a power source, need for setting up and cleaning, loss of drugs during the process of nebulization and inconsistent performances; hygroscopic growth of the aerosol, when produced with a nebulizer, still remains an important issue (Kollef M H, et al, *Intensive Care Med.* 2017, 1-11; Haddrell A E, et al., *Int. J. Pharmaceutics* 2014, 463, 50-61).

On the contrary dry powder inhalers (DPI) are gaining popularity as they are ease to handle, provide better stability of drugs in the solid state and suitable for high dose antibiotics (Lavorini F. et al., *Multidiscip. Respir. Med.* 2017, 12, 11). Some products are available commercially to treat lower respiratory tract infections. Physical properties such as particle size, shape, morphology etc. and stability of the antibiotic powder in DPI formulation play a critical role in the clinical efficacy of the DPIs (Pilcer G et al., *Int. J. Pharma.* 2010, 392, 1-19). These physicochemical properties of the powder formulation can be altered using specialized particle engineering techniques. The two commonly used techniques for producing DPI formulations are spray drying and jet milling. Drug powder particles prepared by 'spray drying' technologies are often preferred as compared those obtained by conventional methods such as 'jet milling' as jet milled particles tend to be cohesive and have high surface energy (Jong T, et al, *J. Pharma. Sci.* 2016, 105, 1156-1163). Spray drying helps to make particles less sticky and achieve better control over particle size.

However, spray drying has limitations for producing inhalation powder formulations as they tend to be amorphous in nature and physically unstable. In our previous studies, we had observed that the spray dried powder of Ciprofloxacin was amorphous in nature and crystallized on storage at the elevated humidity such as at 55% RH and 75% RH, thereby altering the aerosol performance (Shetty N, et al., *Pharm. Res.* 2018, 35, 7). The current study aims to examine the effect of Colistin on the physical stability and aerosolization of the DPI formulations co-spray dried with Ciprofloxacin. Our ultimate goal is to develop a stable spray dried DPI formulation of Ciprofloxacin with Colistin, which would be useful for treating deadly lower respiratory tract infections caused by "resistant" pathogens.

Material and Methods

Chemicals.

Figure 2A:
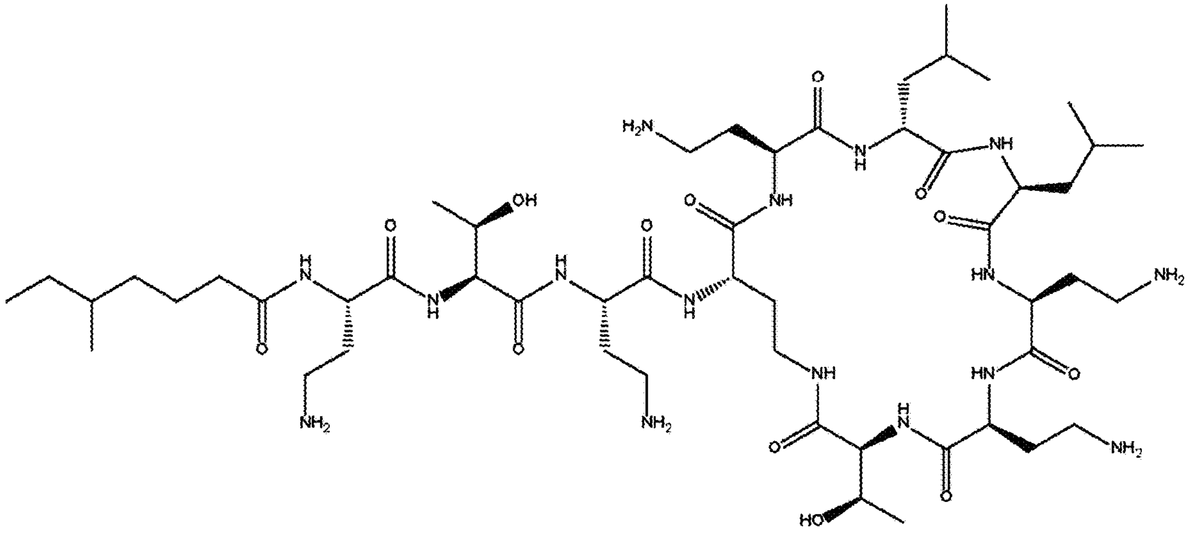
FIG. 2A shows the structure of colistin.
Figure 2B:
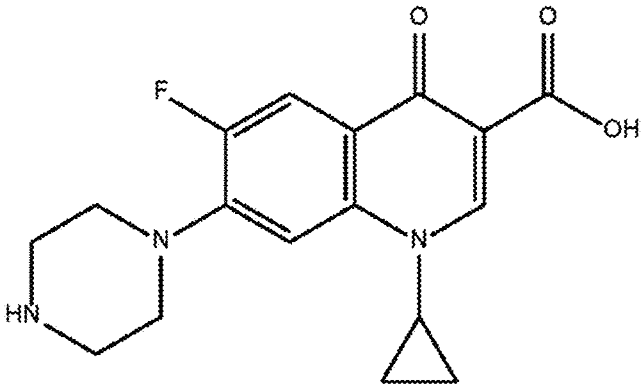
FIG. 2B shows the structure of ciprofloxacin.

Colistin (FIG. 2A) sulfate and Ciprofloxacin (FIG. 2B) hydrochloride monohydrate (abbreviated as Col and Cipro, respectively, in the text) was purchased from ßetaPharma® (Shanghai) Co., Ltd (Wujiang City, JiangSu Province, China). L-leucine (abbreviated as leu in the text) was supplied by Sigma-Aldrich (St. Louis, Mo., USA). Acetonitrile (HPLC grade) and magnesium nitrate was supplied by Fischer scientific (Fair Lawn, N.J., USA).

Spray Drying.

Single and combined powder formulations at different ratios (Table 1) were prepared by spray drying aqueous solution (16 mg/mL total solutes) of Ciprofloxacin hydrochloride and/or Colistin sulfate using a BUCHI B-290 mini spray dryer (BUCHI Labortechnik AG, Flawil, Switzerland). Spray drying was conducted at a feed rate of 2 mL/min with an inlet air temperature ($T_{in}$) of 120±2° C., aspirator at 35 $m^3$/h and airflow of 700 L/h. These conditions resulted in an outlet temperature ($T_{out}$) of approximately 60±2° C. The spray-dried powders were divided into 2 equal parts and stored in a (1) desiccator containing silica gel to maintain 20±2% RH at 20±2° C.; (2) a humidity chamber containing saturated magnesium nitrate solution to maintain 55±2% RH at 20±2° C.

Spray Drying with Leucine:

Single and combined powder formulations at different ratios were prepared by spray drying aqueous solution (16 mg/mL total solutes) of ciprofloxacin hydrochloride and/or colistin sulfate and L-leucine using a BUCHI B-290 mini spray dryer (BUCHI Labortechnik AG, Flawil, Switzerland). Ciprofloxacin hydrochloride and/or colistin sulfate and L-leucine are dissolved in water and this feed solution was pumped into spray dryer nozzle. Spray drying was conducted at a feed rate of 2 mL/min with an inlet air temperature (Tin) of 120±2° C., aspirator at 35 m3/h and airflow of 700 L/h.

Additionally, the co-spray dried ColCipro (1:1) powder formulation was stored at 75%±2% RH at 20±2° C. The co-spray dried formulations were stored at 55% RH for up to two months to determine physical and aerosolization stability and for up to 7 days at 75% RH.

TABLE 1

Compositions of the spray dried formulations.

| | Concentration (% w/w) | | |
|---|---|---|---|
| Formulation | Colistin Sulfate (w/w) | Ciprofloxacin HCl (w/w) | L-leucine (w/w) |
| SD Cipro | 0 | 100 | 0 |
| SD Col | 100 | 0 | 0 |
| co-SD ColCipro (1:1) | 50 | 50 | 0 |
| co-SD ColCipro (1:3) | 25 | 75 | 0 |
| co-SD ColCipro (1:9) | 10 | 90 | 0 |

Powder X-Ray Diffraction (PXRD)

The crystallinity of formulations was evaluated using a Rigaku Smartlab™ diffractometer (Rigaku Americas, Texas, USA). Cu-Kα radiation source and a highly sensitive D/tex ultra-detector at a voltage of 40 kV and current of 44 mA was used. Settings were as follows: 5 to 40° 2θ at a step size of 0.02° with a scan rate of 4°/min.

Particle Size

Particle size distribution of the powder formulation was measured using an Image J software based on SEM images. The diameter at 10% ($d_{10}$), 50% ($d_{50}$) and 90% ($d_{90}$) undersize was calculated for approximately 100 particles, which are sufficient for size measurements of these formulations.

Scanning Electron Microscopy (SEM)

Scanning electron micrographs of the formulations were taken using a NOVA nano SEM (FEI Company, Hillsboro, Oreg., USA). The samples were platinum coated using a sputter coater (208 HR, Cressington Sputter Coater, England, UK) with a current of 40 mA for 1 min. The images were captured at 5 kV.

Dynamic Vapor Sorption (DVS)

Moisture sorption behavior was determined using dynamic vapor sorption (DVS-Intrinsic, Surface Measurement Systems Ltd., London, UK). Each formulation was equilibrated at 0% RH to provide a baseline and then exposed to the different RH. The sorption mass change was measured at RH ranging from 0-90% at 10% RH increments at 25° C. and desorption mass change was measured at RH ranging from 90-0%. At each testing RH moisture content was determined by a dm/dt of 0.002% per minute.

X-ray Photoelectron Spectroscopy (XPS)

Surface composition was quantified using X-ray photoelectron spectroscopy (XPS) (AXIS Ultra DLD spectrometer, Kratos Analytical Inc., Manchester, UK) with monochromic Al Kα radiation (1486.6 eV) at pass energy (PE) of 20 and 160 eV for high-resolution and survey spectra, respectively. A commercial Kratos charge neutralizer was used to avoid non-homogeneous electric charge of non-conducting powder (in this case, the powders were conducting) and to achieve better resolution. Typical instrument resolution for pass energy (PE) of 20 eV is ~0.35 eV. Binding energy (BE) values refer to the Fermi edge and the energy scale was calibrated using Au 4f7/2 at 84.0 eV and Cu 2p3/2 at 932.67 eV. Powder samples were placed on a stainless-steel sample holder bar using a double-sided sticking Cu tape. XPS data were analyzed with CasaXPS software version 2313 Dev64. Prior to data analysis, the C—C component of the C 1s peak was set to a binding energy of 284.8 eV to correct for charge on each sample. Curve-fitting was performed following a Shirley background subtraction using model peaks obtained from pure compounds. The atomic concentrations of the elements in the near-surface region were estimated after a Shirley background subtraction taking into account the corresponding Scofield atomic sensitivity factors and inelastic mean free path of photoelectrons using standard procedures in the CasaXPS software assuming homogeneous mixture of the elements within the information depths (~10 nm).

Energy Dispersive X-ray Spectrometer (EDX)

EDX was used to map the distributions of Colistin (presence of sulphur) and Ciprofloxacin (presence of chlorine) in the powder formulations (ULTRA plus, Zeiss, Germany). For each measurement, the beam was focused on the single particles. Ten to fifteen EDX measurements were acquired from each sample at an accelerating voltage of 7 kV and the images were captured at a working distance of ~10 mm. The electron beam energy influences the penetration depth into the surface, which is in the range of a few micrometers and was kept constant for all measurements. The emitted X-rays were detected by x-act detector (Oxford instruments, Oxfordshire, UK) and were analyzed using the Aztec® EDX analysis software.

Time-of-Flight Secondary Ion Mass Spectrometry (ToF-SIMS)

The surface distributions of different components in the spray-dried composite formulations were evaluated using Time-of-flight secondary ion mass spectrometry (ToF-SIMS, TRIFT V nanoToF, Physical Electronics Inc., Chanhassen, Minn., USA). The detailed descriptions were described elsewhere (25). Mass resolution for spectra was optimized by the "bunched" Au1 instrumental settings, while spatial resolution was optimized by "unbunched" Au1 instrumental settings for the Collection of images. ToF-SIMS data were collected from 5 areas (75×75 μm each) for each sample. Characteristic mass fragments were identified to effectively discern surface Colistin, Ciprofloxacin and leucine signals. The unique characteristic mass fragment selected for Colistin was at m/z 86 atomic mass unit (amu) corresponding to [$C_5Hi_2N^+$], Ciprofloxacin was at m/z 101 amu corresponding to [$C_4H_9N_2O^+$] and l-leucine was at m/z 132 amu corresponding to [$C_6H_{14}NO_2^+$]. The spectra were integrated, and high-resolution surface composition overlays were constructed using WincadenceN software (Physical Electronics Inc., Chanhassen, Minn., USA).

Drug Quantification

Drug concentration for Ciprofloxacin hydrochloride and Colistin sulfate was determined by high performance liquid chromatography (HPLC) using 76% v/v of 30 mM solution of sodium sulfate (adjusted to pH 2.5 with $H_3PO_4$) and 24% v/v acetonitrile as mobile phase resulting in isocratic elution of the sample with a retention time of 8 minutes at a flow rate of 1.0 mL/min. Briefly, the HPLC system consisted of G1311C (1260 Quat Pump VL) pump, G1330B (1290 Thermostate) thermostate, G1329B (1260 ALS) autosampler, G1316A (1260 TCC) thermostated column compartment, G1314F (1260 VWD) variable wavelength detector (Agilant, Waldbronn, Germany), and an Agilant Eclipse Plus, 5 μm C18 150×4.60 mm column (Agilant, Waldbronn, Germany). The calibration curve for Ciprofloxacin hydrochloride was linear ($r^2$>0.99) over the concentration range of approximately 0.22 to 0.006 mg/mL. Calibration curve for Colistin sulfate was linear ($r^2$=1) over the concentration range of approximately 0.5 to 0.006 mg/mL.

In-Vitro Aerosol Performance

A Multi-Stage Liquid Impinger (MSLI) (Copley Scientific Limited, Nottingham, UK) with a USP induction port (USP throat) was used to determine in-vitro aerosol performance of the spray dried formulations. Each formulation (10±1 mg) was filled into a size 3 hydroxypropyl methylcellulose capsule (Qualitycap, Whitsett, N.C., USA) and dispersed through aRS01 DPI device. A standard dispersion procedure (USP 38) was carried out by passing 4 L of air through the inhaler at an airflow of 100 L/min for 2.4 s, with a pressure drop of approximately 4 kPa at 100 L/min across the device. The cutoff diameters for Stages 1-4 of the liquid impinger at 100 L/min were 10.4, 4.9, 2.4, and 1.2 μm, respectively. Four replicated experiments were carried out for the powder formulations stored at ≤20% and 55% relative humidity conditions, and each experiment comprised sequential dispersion of two filled capsules. Drug particles deposited in the capsule, inhaler device, USP throat, Stage 1-4 and the filter paper in the impactor base were collected using MilliQ water. Drug contents were analyzed using a validated high-performance liquid chromatography (HPLC) method described above. The emitted dose was determined as the drug released from the capsule and device; whereas the fine particle fraction was defined as particles with an aerodynamic size below 4.9 μm (cut-off diameter of Stage 2) relative to the total recovered drug.

Statistical Analysis.

Statistical analysis was performed by one-way analysis of variance (ANOVA) with Tukey-Kramer post hoc tests using a GraphPad Prism Software (GraphPad Software, Inc., La Jolla, Calif.). Probability values of less than 0.05 were considered as a statistically significant difference and "NS" represents not significant ($p>0.05$).

Physical Stability and Aerosol Performance of Co-Spray Dried Formulation at 55% Relative Humidity (RH)

PXRD.

Figure 1B:
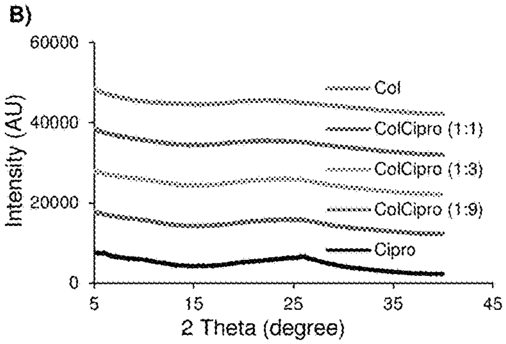
Figure 1C:
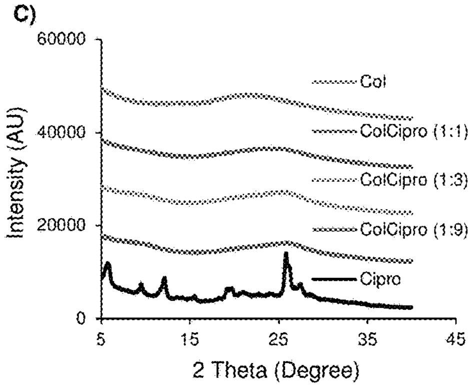
Figure 1D:
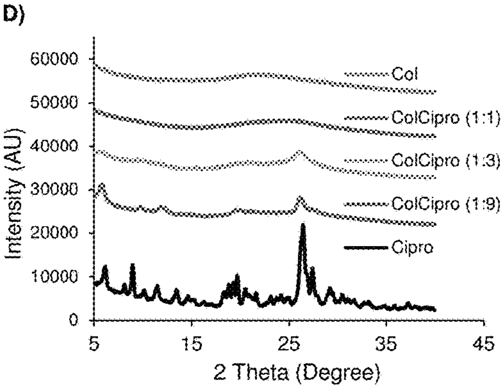
Figure 1E:
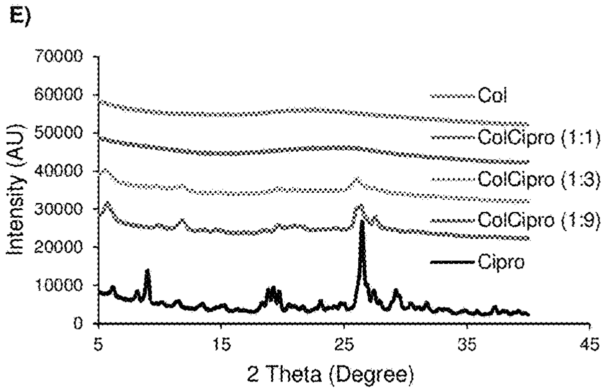

PXRD patterns depict that the spray dried Ciprofloxacin alone, spray dried Colistin and co-spray dried ColCipro powder formulations with different mass ratios were amorphous upon spray drying (FIG. 1A) and did not show any crystallization up to 60 days when stored at 20% RH (FIG. 1B). However, the spray dried Ciprofloxacin particles crystallized upon one-day storage at 55% RH but all other formulations were amorphous after one day storage at 55% RH (FIG. 1C). The co-spray dried ColCipro formulation in the mass ratio (1:3) and (1:9) crystallized at Day 3 upon storage at 55% RH (FIG. 1D). But, the co-spray dried ColCipro formulation in the mass ratio (1:1) was amorphous up to 60 days upon storage at 55% RH (FIG. 1E). The PXRD data indicated that incorporation of Colistin in the formulation inhibited the crystallization of Ciprofloxacin upon storage at 55% RH. Crystallization of Ciprofloxacin was prevented when co-spray dried with Colistin in the mass ratio (1:1) and stored at 55% RH for up to 60 days.

TABLE 2

Particle size distribution for SD Cipro, SD Col and co-spray dried ColCipro formulation in the mass ratio (1:1), (1:3) and (1:9) stored at 20% RH for 3 days

| Formulation | $D_{10}$ (μm) | $D_{50}$ (μm) | $D_{90}$ (μm) |
|---|---|---|---|
| Ciprofloxacin | 0.39 | 0.99 | 2.07 |
| ColCip (1:1) | 0.74 | 1.26 | 2.18 |
| ColCip (1:3) | 0.63 | 1.21 | 2.05 |
| ColCip (1:9) | 0.47 | 1.04 | 2.10 |
| Colistin | 0.81 | 1.30 | 2.40 |

TABLE 3

Particle size distribution for SD Cipro, SD Col and co-spray dried Col-Cipro formulation in the mass ratio (1:1), (1:3) and (1:9) stored at 55% RH for 3 days

| Formulation | $D_{10}$ (μm) | $D_{50}$ (μm) | $D_{90}$ (μm) |
|---|---|---|---|
| Ciprofloxacin | 0.19 | 1.24 | 2.42 |
| ColCip (1:1) | 0.64 | 1.21 | 2.00 |
| ColCip (1:3) | 0.62 | 1.19 | 2.05 |
| ColCip (1:9) | 0.47 | 1.00 | 1.98 |
| Colistin | 0.81 | 1.35 | 2.27 |

Particle Size.

Tables 2 and 3 shows the physical particle size distribution of SD Cipro, SD Col and co-spray dried ColCipro formulations in the mass ratio (1:1), (1:3) and (1:9) stored at 20% and 55% RH respectively. No remarkable difference in physical particle size was observed for 5 different formulations stored at 20% and 55% RH. All 5 different formulations were shown to have fine physical size with $D_{90}<3$ μm.

Surface Morphology

Figure 3:
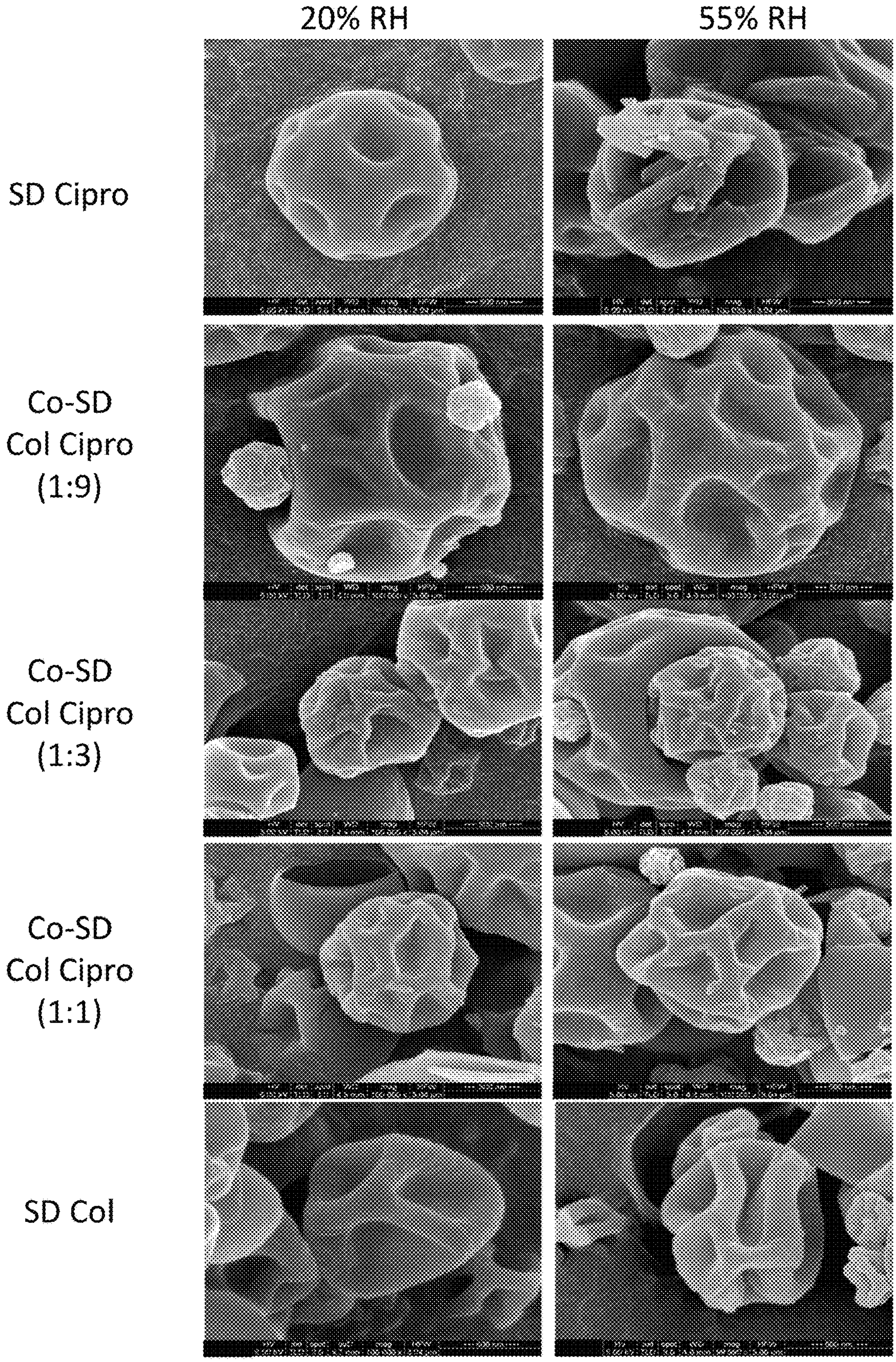
FIG. 3 depicts various SEM images of the drug alone and co-spray dried Colistin-Ciprofloxacin powder formulations stored at 20% and 55% RH for 3 days.
Figure 4A:
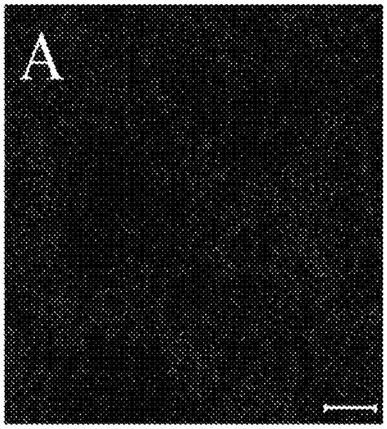
FIGS. 4A-4E show surface composition distributions of Colistin (red) and Ciprofloxacin (green) on the surfaces of composite particles obtained by ToF-SIMS.
Figure 4B:
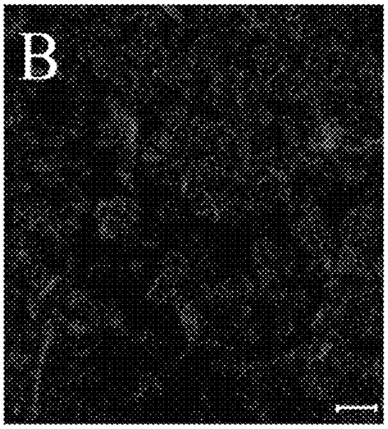
Figure 4C:
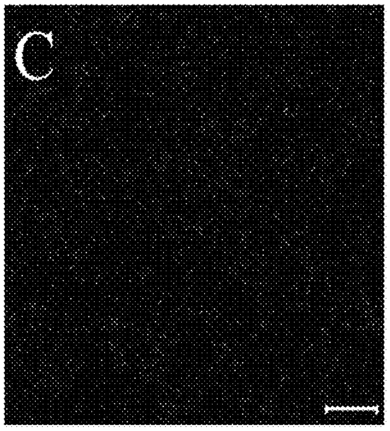
Figure 4D:
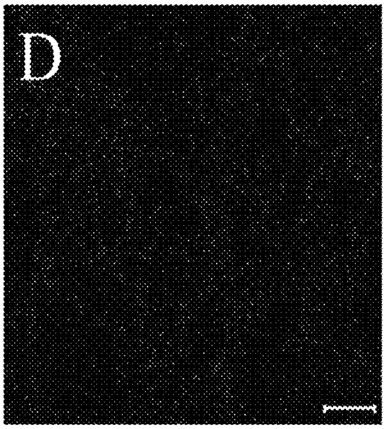
Figure 4E:
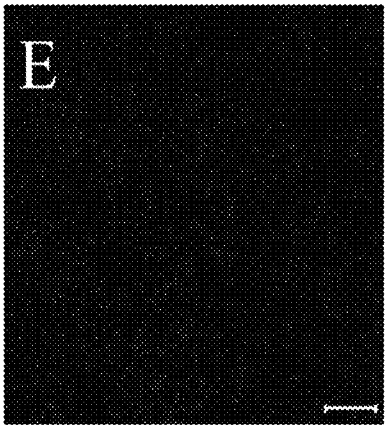

SEM images of the spray dried Ciprofloxacin alone, spray dried Colistin alone and co-spray dried powder formulations at different concentrations stored at 20% RH and 55% RH for 3 days are shown in FIG. 3. The SD Ciprofloxacin alone formulation stored at 20% RH had a smooth dimpled surface with spherical shape; but at 55% RH for 3 days, the particles were rougher which is in good agreement to our previous finding (25), attributed to crystallization of amorphous spray dried Ciprofloxacin particles. On the other hand, the spray dried Colistin formulation stored at 20% and 55% RH had a smooth surface with an irregular shape (FIG. 3). No change in morphology of the spray dried Colistin when stored at two RHs, which is in agreement with no change in amorphous form (FIG. 1D) Similarly, no change in morphology was observed for the co-spray dried formulations at different concentrations stored at two different RHs. The co-spray dried formulations of ColCipro in the mass ratio (1:1), (1:3) and (1:9) had a smooth surface with spherical shape upon storage at both 20% and 55% RH (FIG. 3). Thus, although co-spray dried formulation in the mass ratio (1:3) and (1:9) crystallized after three days of exposure to 55% RH, no change in particle morphology was observed.

Energy Dispersive X-ray Spectroscopy (EDX).

Figure 5:
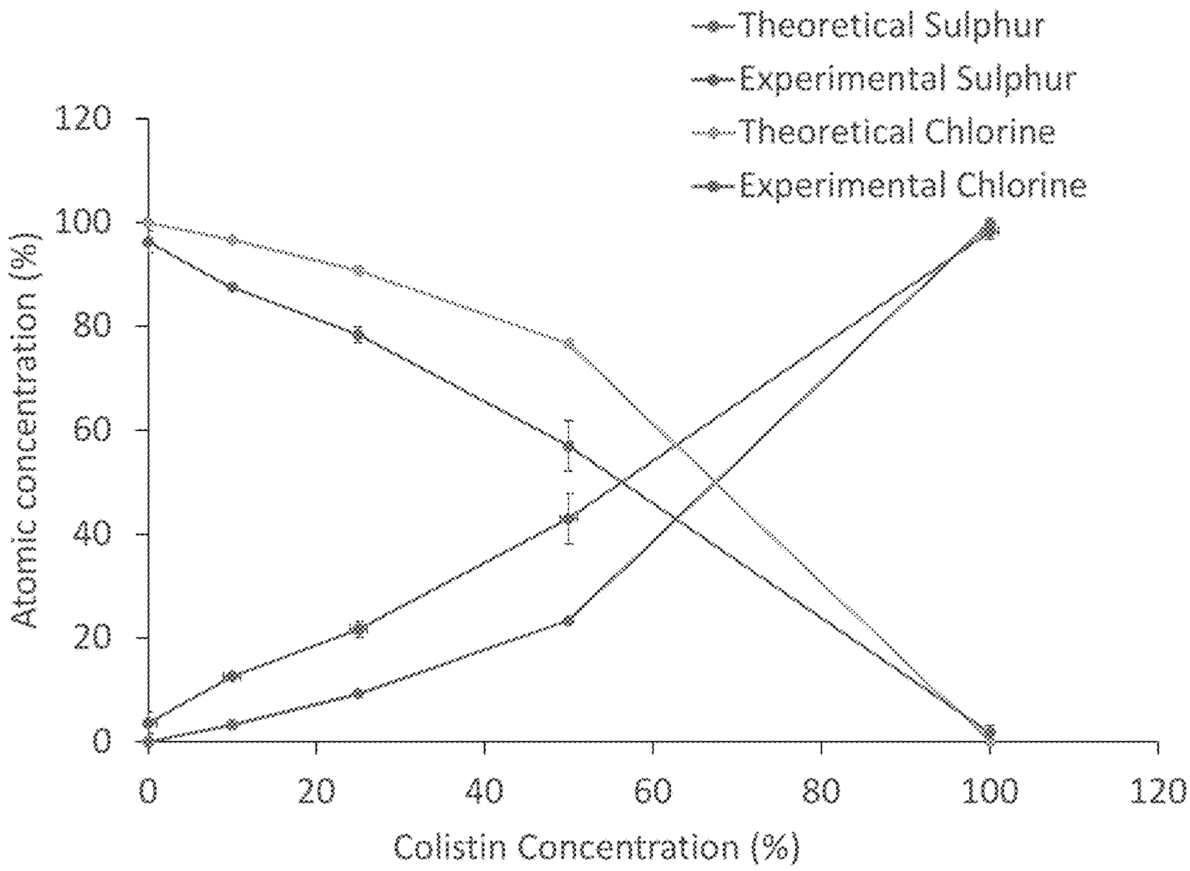
FIG. 5 depicts surface concentrations based on elemental analysis of chlorine (in Ciprofloxacin hydrochloride) and sulphur (in Colistin sulfate) measure by EDX.

FIG. 5 depicts quantitative surface coverage of the elements in the co-spray dried formulations. Theoretical atomic concentration of sulfur in the co-spray dried ColCipro formulation (1:9) was found to be 3.27% whereas the experimental atomic concentration was found to be 12.5±0.5%. Experimental sulphur (Colistin) concentration was greater than theoretical value in the co-spray dried formulations for all different mass ratios indicating surface enrichment of Colistin in these combination formulations.

X-Ray Photoelectron Spectroscopy (XPS).

Table 4 shows surface compositions of two drugs in the co-spray dried formulations measured by XPS. 74% of Colistin and 26% of Ciprofloxacin carbon composition from XPS differed significantly from the theoretical carbon composition for Colistin (50%) and Ciprofloxacin (50%) in Colistin-Ciprofloxacin (1:1) co-spray dried formulation. Likewise, Colistin (60%) and Ciprofloxacin (40%) carbon composition from XPS differed significantly from the theoretical carbon composition for Colistin (25%) and Ciprofloxacin (75%) in Colistin-Ciprofloxacin (1:3) co-spray dried formulation. Even when both the drugs were present at 50% the Colistin composition from XPS was 74%. Thus, for all 3 formulations the practical surface composition for Colistin was significantly higher than the theoretical surface composition indicating higher surface coverage by Colistin in the co-spray dried Colistin-Ciprofloxacin formulation.

TABLE 4

Theoretical and surface composition from XPS (% mass ratio) based on number of carbon atoms for the co-spray dried Colistin-Ciprofloxacin formulations in different mass ratios.

| | Theoretical Surface Composition (%) | | Measured Surface Composition (%) | |
|---|---|---|---|---|
| Formulations | Colistin | Ciprofloxacin | Colistin | Ciprofloxacin |
| ColCipro_1:9 | 10 | 90 | 35 | 65 |
| ColCipro_1:3 | 25 | 75 | 60 | 40 |
| ColCipro_1:1 | 50 | 50 | 74 | 26 |

Dynamic Vapor Sorption

Figure 6A:
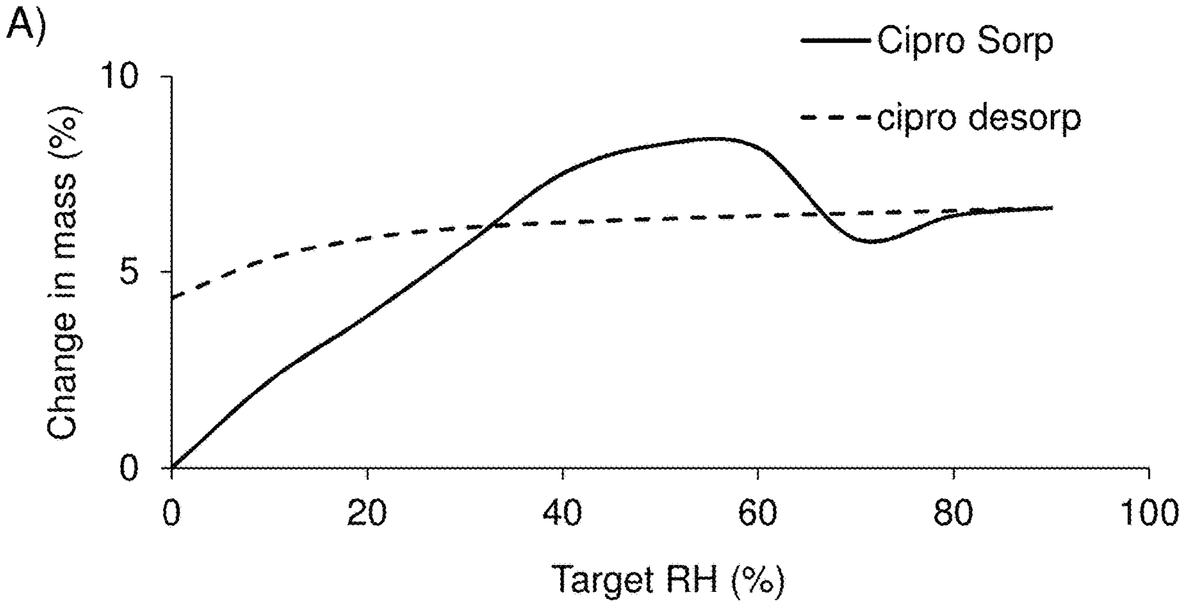
Figure 6B:
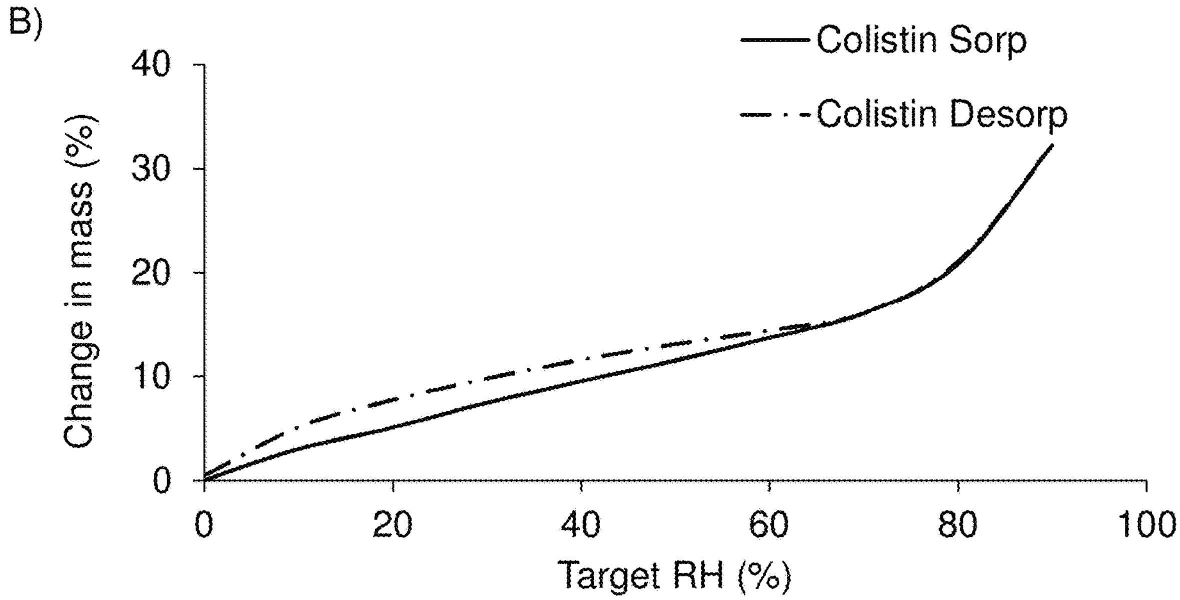
Figure 6C:
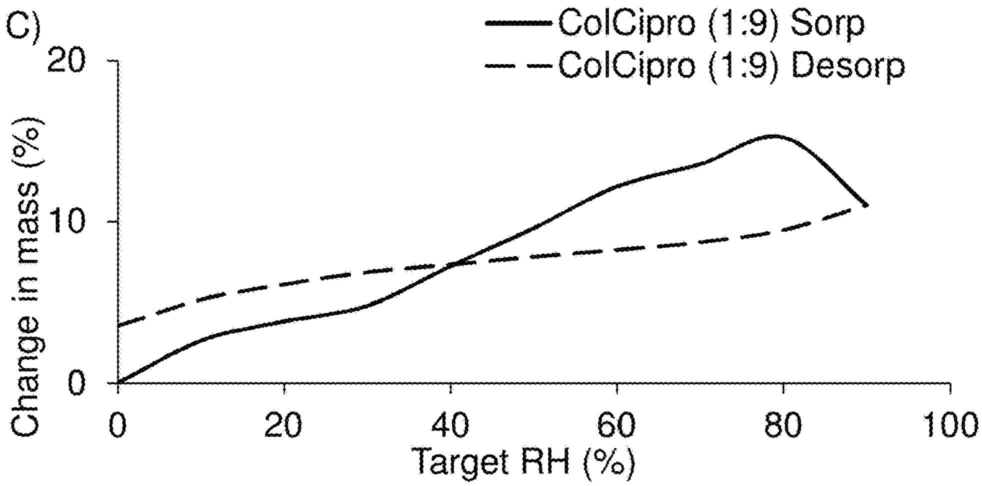
Figure 6D:
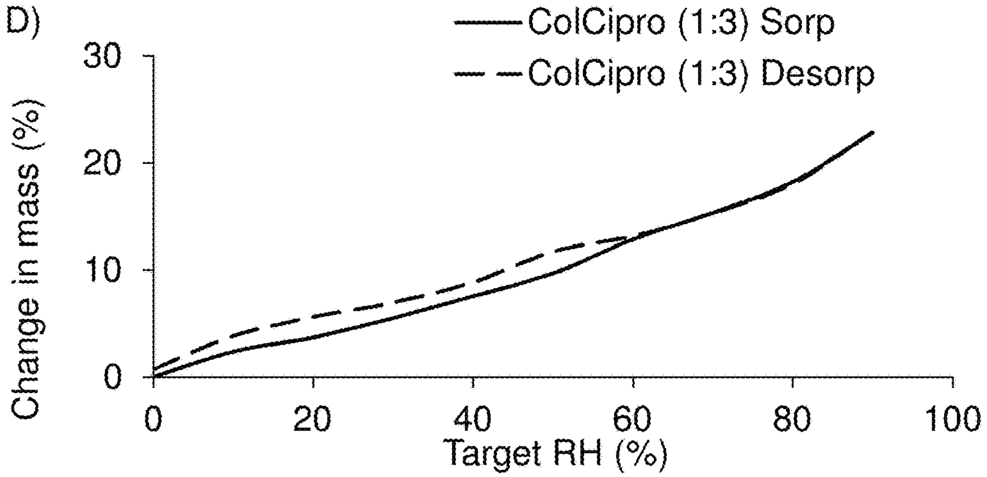
Figure 6E:
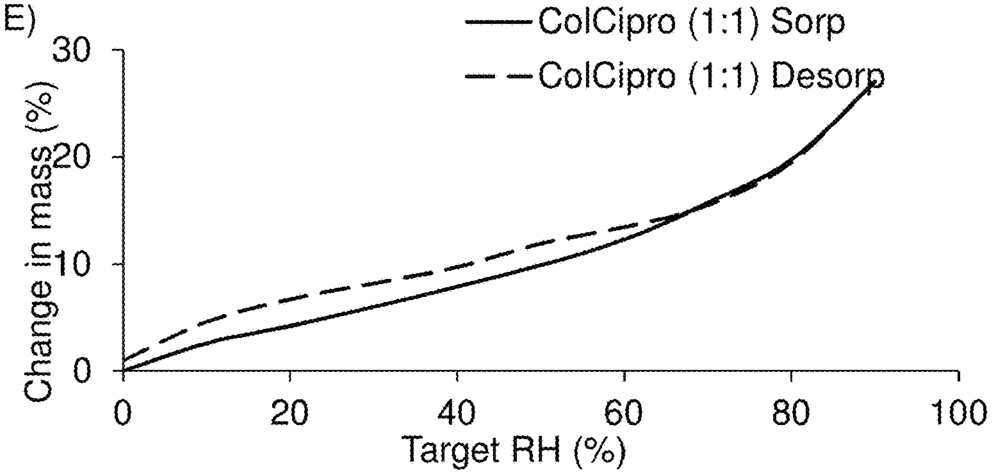

The sorption and desorption profiles for Colistin, ColCip (1:1) and ColCip (1:3) formulations were similar with no evidence of recrystallization or permanent retention of water, which are in accordance with our hypothesis that Colistin prevents crystallization of Ciprofloxacin when exposed to moisture (FIGS. 6B, 6D & 6E). However, for the ColCip (1:9) formulation it showed a tendency to crystallize at a humidity of approx. 80% and retention of water in the sample at the end of the measurement of 0% RH (FIG. 6C). The spray dried Ciprofloxacin alone formulation has shown to absorb much less moisture in comparison to spray dried Colistin beyond approximately 70% RH (30) (FIG. 6A).

In-Vitro Aerosol Performance of Co-Spray Dried Formulations.

Figure 7A:
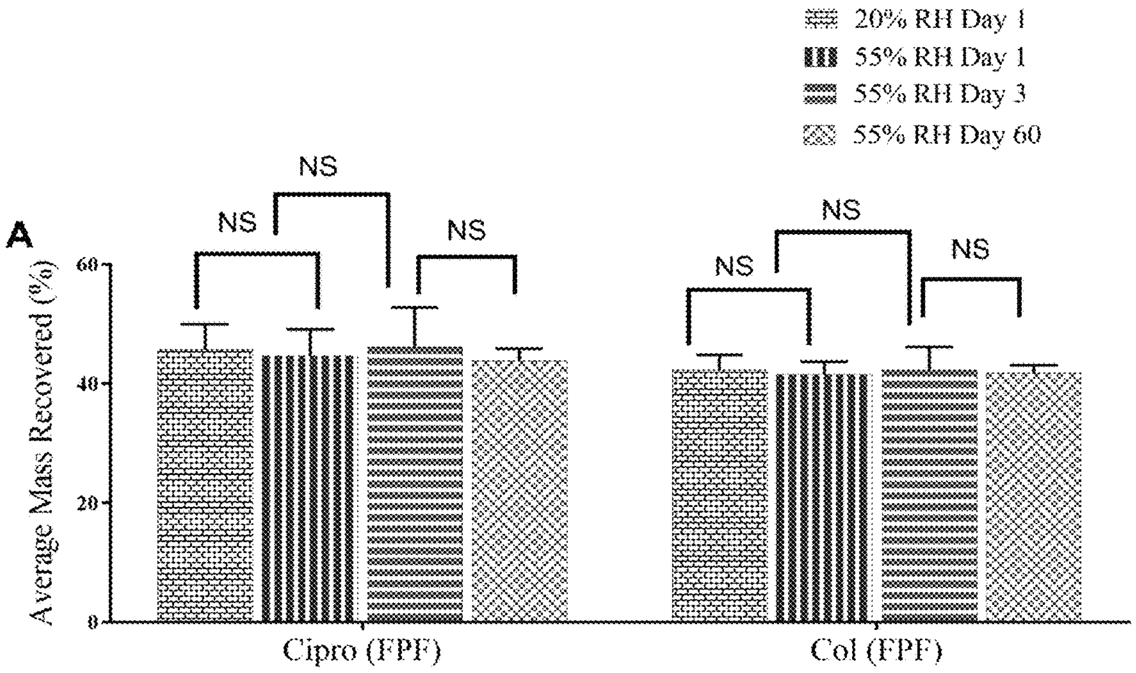
FIGS. 7A-7C show in-vitro aerosol performance of Ciprofloxacin and Colistin in the co-spray dried formulations at different mass ratios.
Figure 7B:
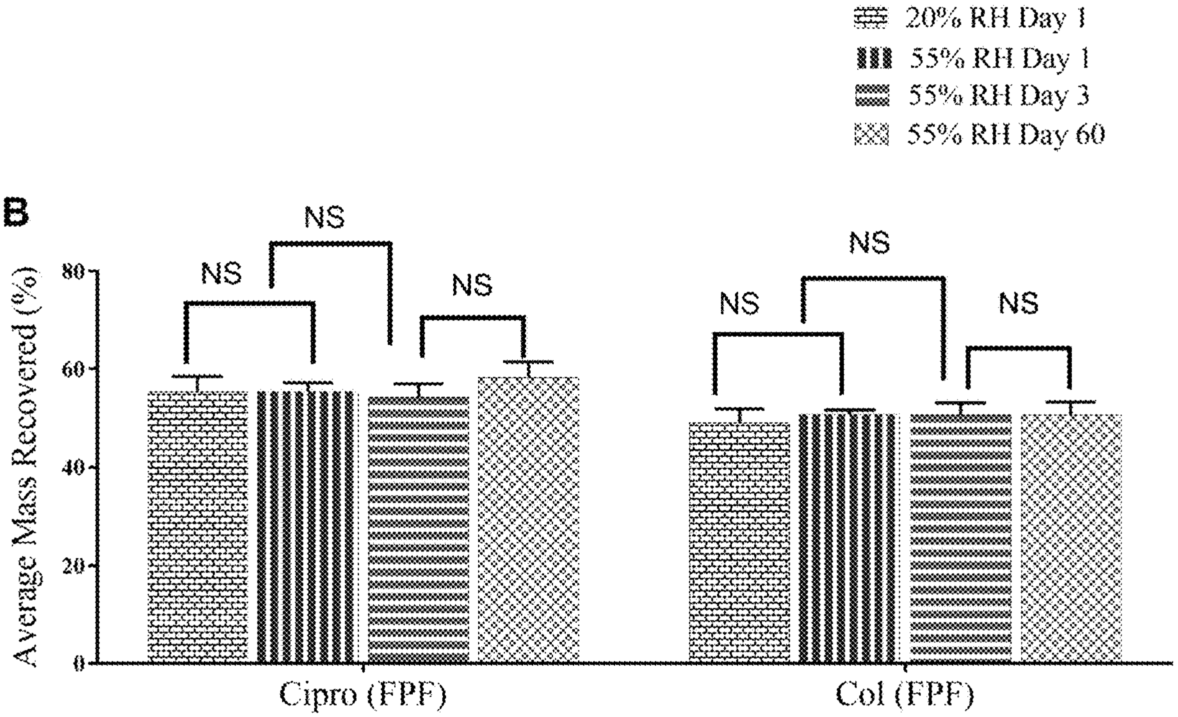
Figure 8:
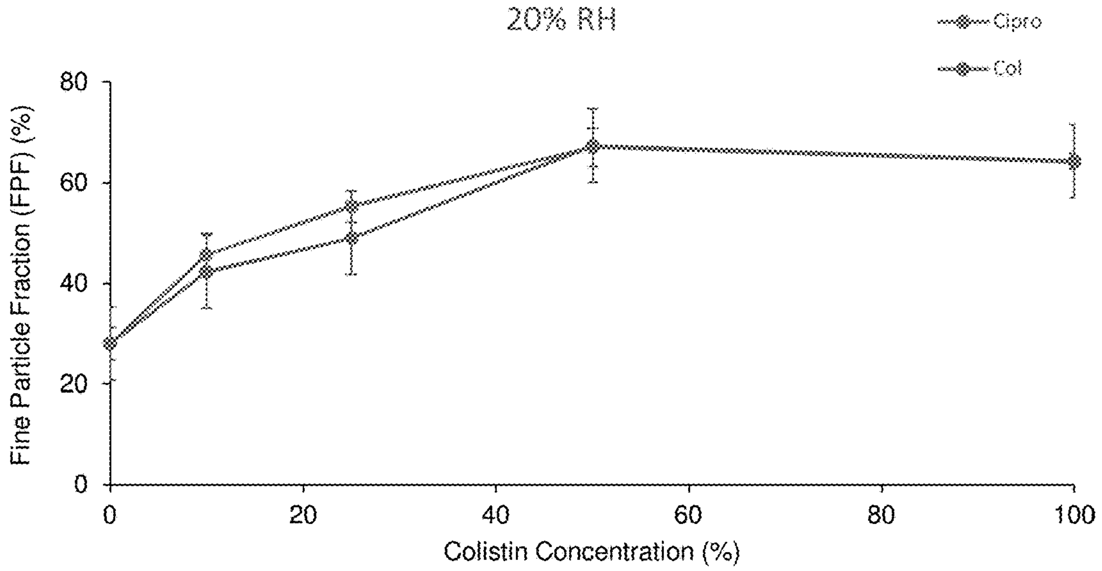
FIG. 8 shows the effect of Colistin concentration on aerosol performance of co-spray dried formulation after storage at 20% RH for 1 day (mean±SD, n=4; *, p<0.05; , p<0.01; *, p<0.001; ****, p<0.0001; NS, no significant difference).

Thus, co-spray drying Ciprofloxacin with Colistin inhibits crystallization of amorphous Ciprofloxacin and ensured stability in terms of aerosol performance. Additionally, an increase in aerosol performance of Ciprofloxacin was measured by increasing Colistin concentration from 10% to 50% (FIG. 8). The aerosol performance of co-spray dried Colistin-Ciprofloxacin formulation in the mass ratio (1:9) was significantly higher ($p<0.0001$) compared to the spray dried Ciprofloxacin alone (28±3.2). Aerosol performance for the ColCip (1:3) (55.3±3.1) and ColCip (1:1) (67.1±3.8) showed further significant increases ($p<0.01$) as compared to the ColCip (1:9) (45.7±4.2). Even for the ColCip (1:9) and ColCip (1:3), in which crystallization was observed after 3 days, no significant change was measured in the aerosol performance (FIGS. 7A and 7B).

Change in Morphology Upon Long-Term Storage

Figure 9:
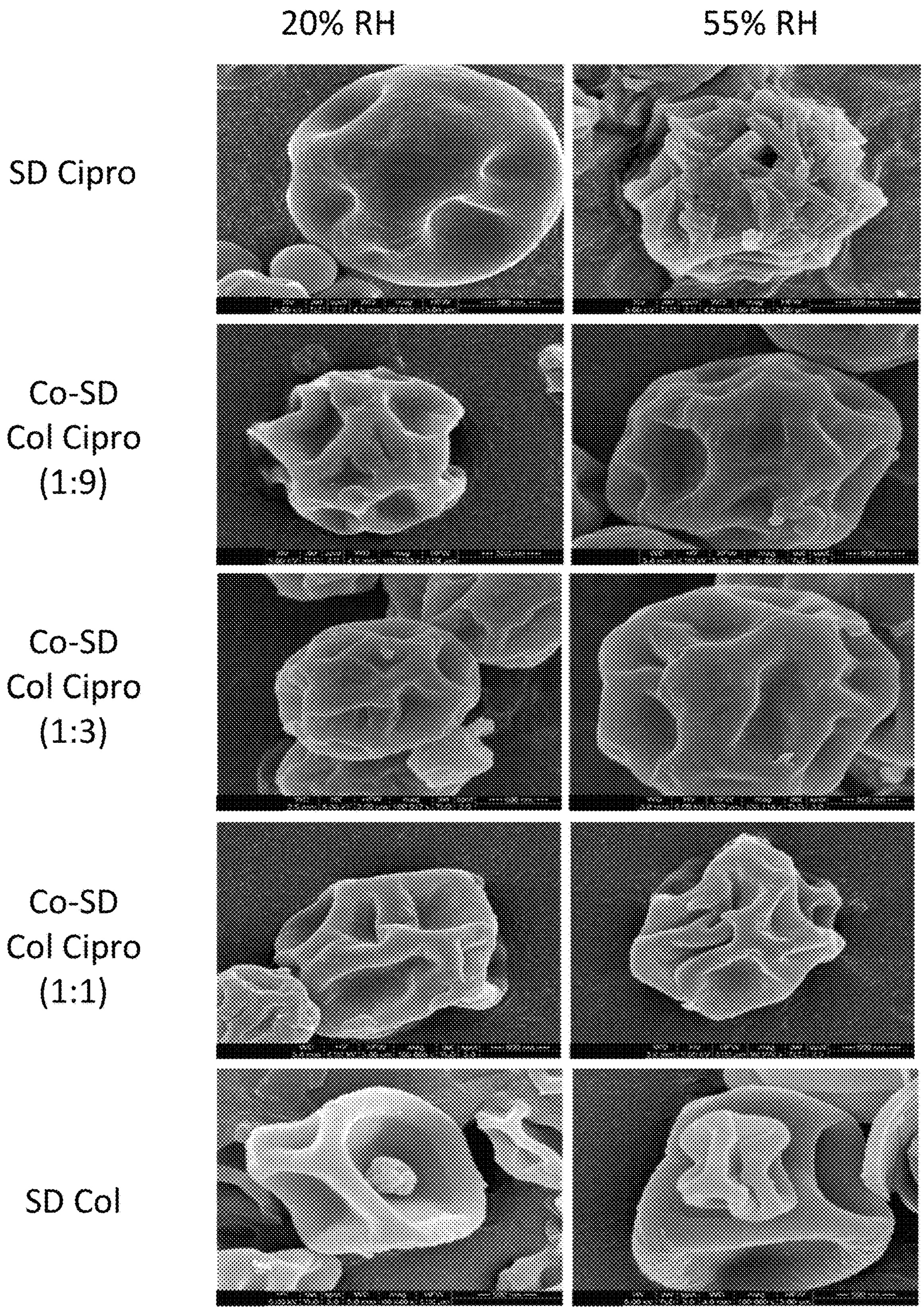
FIG. 9 shows SEM images of spray dried formulations at 20% and 55% RH for 60 days.

SEM images of the spray dried Ciprofloxacin alone, spray dried Colistin alone and co-spray dried powder formulations stored at 20% RH and 55% RH for 60 days are shown in FIG. 9. The round dimpled shaped spray dried Ciprofloxacin powder formulation underwent a drastic change to rough particles upon storage at 55% RH after 3 days (FIG. 3) and retained that rough surface for up to 60 days at 55% RH (FIG. 9). However, there was no significant change in particle morphology with the co-spray dried Colistin-Ciprofloxacin formulation in the mass ratio (1:1), (1:3) and (1:9) stored at 55% RH for 60 days as compared to the corresponding formulations stored at 20% RH. Also, no change in particle morphology was observed for the spray dried Colistin alone stored at 55% RH for 60 days as compared to that stored at 20% RH.

Physical Stability and Aerosol Performance of the Co-Spray Dried Formulation (1:1) at 75% RH Since the co-spray dried Colistin-Ciprofloxacin formulation in the mass ratio (1:1) was found to be amorphous at 55% RH for 60 days with no change in surface morphology or aerosol performance we further investigated the performance of this formulation at 75% RH.

PXRD.

Figure 10:
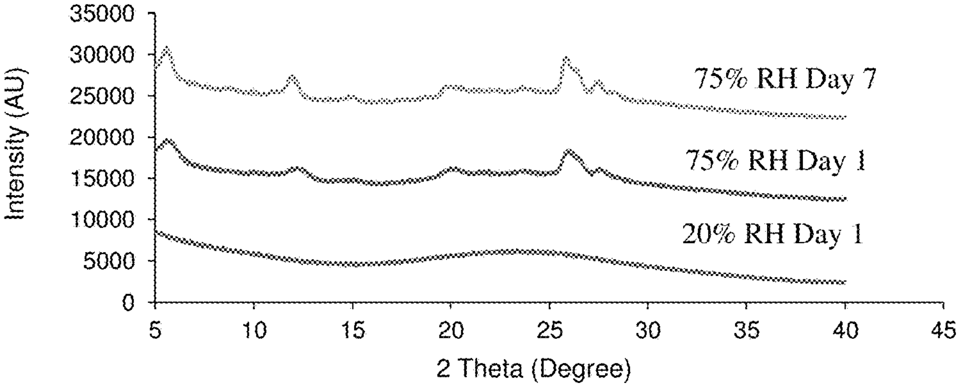
FIG. 10 demonstrates PXRD patterns for the co-spray dried Ciprofloxacin-Colistin formulation in the mass ratio (1:1) stored at 75% RH for up to 7 days.

FIG. 10 depicts the PXRD patterns for the co-spray dried Ciprofloxacin-Colistin formulation in the mass ratio (1:1) upon storage at 75% RH for 7 days. The co-spray dried Ciprofloxacin-Colistin formulation at 20% RH is amorphous; however ciprofloxacin crystallized upon exposure to 75% RH after 1 day. A subsequent increase in degree of crystallization was observed from day 1 to day 7 for the co-spray dried Ciprofloxacin-Colistin formulation at 75% RH; although such increase was marginal. We further investigated the effects of such crystallization on the surface morphology and aerosol performance of the co-spray dried formulation.

Scanning Electron Microscopy (SEM)

Figure 11A:
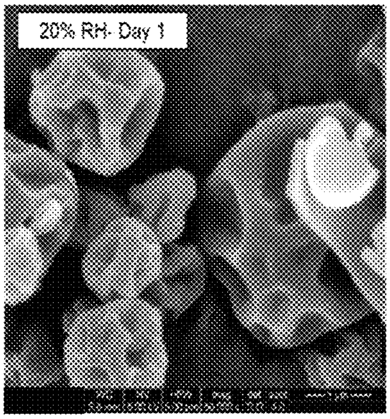
FIG. 11A shows SEM micrographs for the co-spray dried Ciprofloxacin-Colistin formulation in the mass ratio (1:1) stored at 20% RH at Day 1.
Figure 11B:
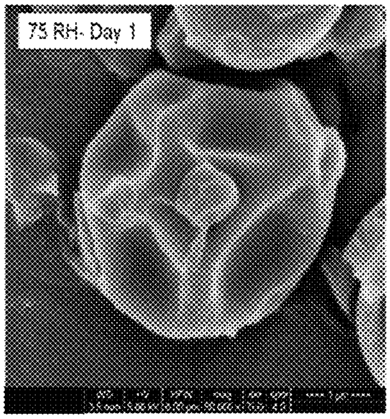
FIG. 11B shows SEM micrograph for the co-spray dried Ciprofloxacin-Colistin formulation in the mass ratio (1:1) stored at 75% RH at Day 1.
Figure 11C:
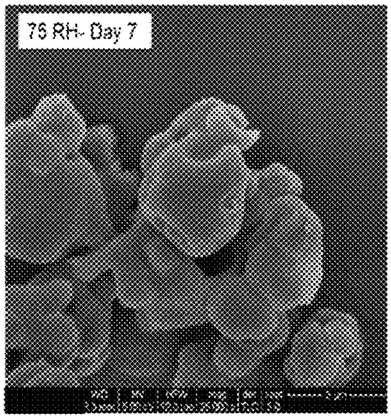
FIG. 11C shows SEM micrograph for the co-spray dried Ciprofloxacin-Colistin formulation in the mass ratio (1:1) stored at 75% RH at Day 7.

The co-spray dried Ciprofloxacin-Colistin formulation had a smooth surface with spherical shape at 20% RH. No change in surface morphology of the co-spray dried formulation was observed upon storage at 75% RH for one day. However, upon storage at 75% RH for 7 days, the powders appeared to be fused (FIGS. 11A-11C). Based on the XPS data (Table 4) we observed that Colistin is enriched at the surface of the co-spray dried Ciprofloxacin-Colistin formulation in the mass ratio (1:1) and it has been studied previously that Colistin has a greater tendency to absorb moisture (30).

Figure 12:
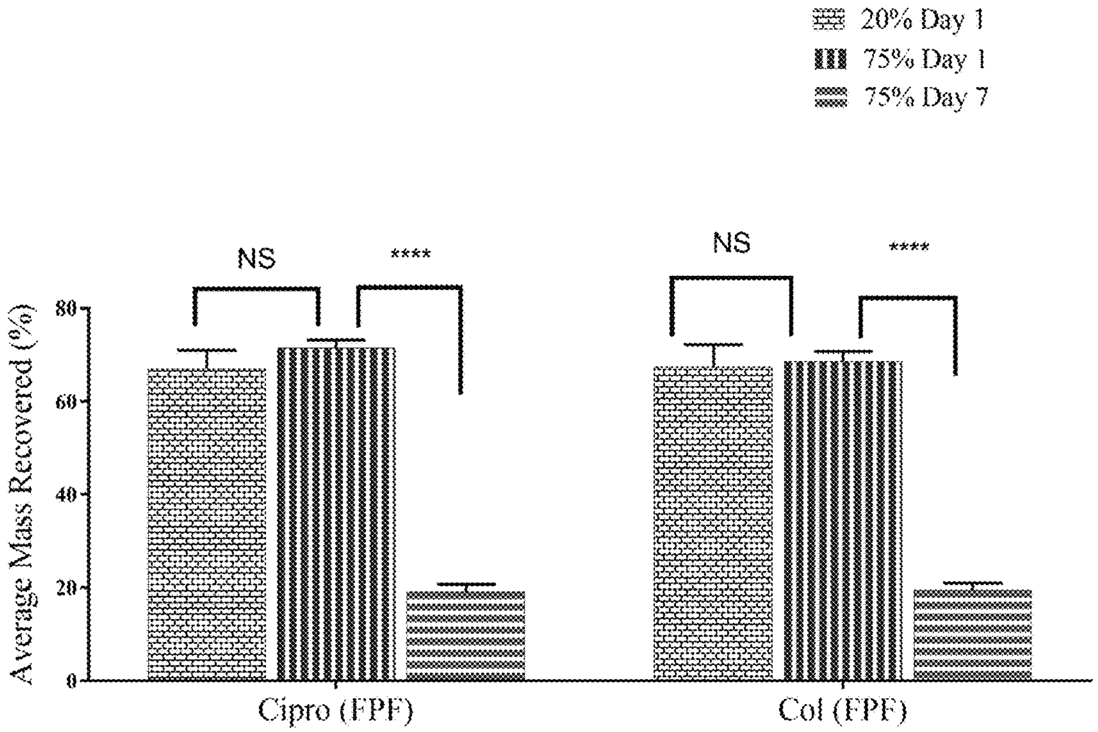
FIG. 12 shows In-vitro aerosol performance of Ciprofloxacin and Colistin in the co-spray dried formulation with mass ratios (1:1) stored at 75% RH for 7 days (mean±SD, n=4; ****, p<0.0001; NS, no significant difference)

In-vitro Aerosol Performance. Upon storage at 75% RH for one day no significant change ($p>0.05$) in FPF for both Colistin (68.6±2.1%) and Ciprofloxacin (71.5±1.7%) was observed as compared to the FPF of both Colistin (67.4±4.9%) and Ciprofloxacin (67.1±3.8%) at 20% RH for 1 day. However, a significant decrease ($p<0.0001$) in FPF was observed when the co-spray dried Ciprofloxacin-Colistin formulation was stored at 75% RH for 7 days (FIG. 12). The FPF for Ciprofloxacin and Colistin decreased to 19.2±1.4% and 19.5±1.3% respectively when stored at 75% RH for 7 days. As previous studies showed that co-spray drying with leucine may minimize the negative effects of moisture on aerosolization. Thus, we add L-leucine in the formulation in order to prevent such moisture effects (Li L., et al., *Eur. J. Pharm. Biopharm.* 2016, 102, 132-141).

Enhancing Physical and Aerosolization Stability by Adding L-Leucine

PXRD.

Figure 13:
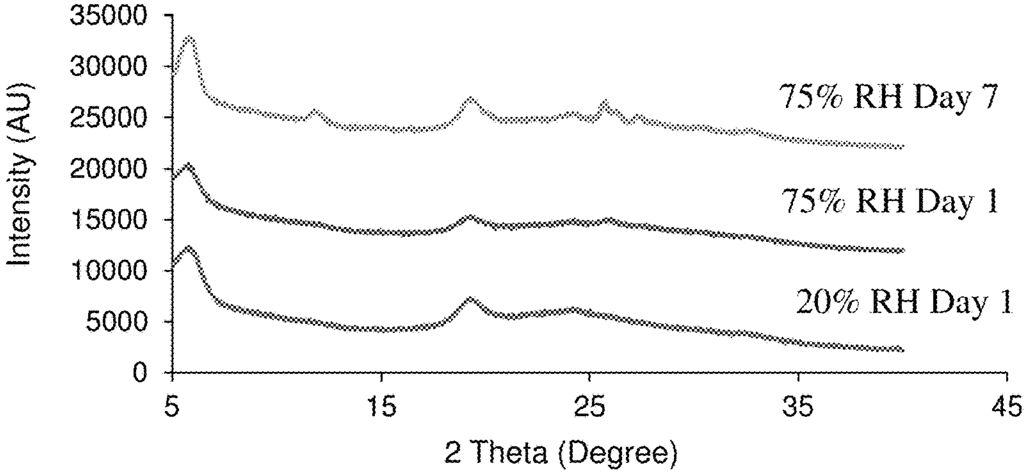
FIG. 13 shows PXRD patterns for the co-spray dried Colistin-Ciprofloxacin-leucine (ColCipLeu) formulation in the mass ratio (1:1:1) stored at 75% RH for up to 7 days.

FIG. 13 depicts the PXRD patterns for the co-spray dried Colistin-Ciprofloxacin-leucine (ColCipLeu) formulation in the mass ratio (1:1:1) upon storage at 75% RH for 7 days. The co-spray dried ColCipLeu (1:1:1) formulation at both 20% RH and 75% RH was found to be crystalline at day 1. Interestingly, no ciprofloxacin peaks were observed at day 1 as seen with ColCipro co-spray dried formulations stored at 75% RH for 1 day (FIG. 10). However, the crystalline peaks corresponded to the spray dried leucine. Upon storage at 75% RH for 7 days, slight crystallization of drug Ciprofloxacin was observed for the co-spray dried ColCipLeu (1:1:1) formulation.

SEM.

The co-spray dried Colistin-Ciprofloxacin-leucine formulation in the mass ratio (1:1:1) had a dimpled and rough surface with a near spherical shape at 20% RH. No change in morphology of the co-spray dried formulation was observed upon storage at 75% RH for 7 days (FIGS. 14A-14C).

In-Vitro Aerosol Performance.

FIG. 15 depicts the in-vitro aerosol performance for co-spray dried ColCipLeu formulation in the mass ratio (1:1:1) stored at 20% RH for 1 day, 75% RH for 1 day and 7 days respectively. FPF for both Colistin (62.9±6.1%) and Ciprofloxacin (63.1±4.7%) stored at 75% RH for 1 day did not change significantly as compared to the FPF of both Colistin (58.7±2.2%) and Ciprofloxacin (62.1±2.2%) at 75% RH for 7 days. Adding L-leucine prevented change in surface morphology and aerosol performance upon storage of this formulation at 75% RH for up to 7 days.

X-Ray Photoelectron Spectroscopy (XPS)

The measured Leucine surface concentration (44%) was much higher than the theoretical Leucine concentration (33%) in the ColCipLeu (1:1:1) co-spray dried powder formulation (Table 5). Measured surface Ciprofloxacin (22%) was significantly lower than the theoretical (33%). While measured (34%) and theoretical (33%) surface Colistin concentration was nearly identical. Both Colistin and leucine are known to be surface active agents however, based on the XPS data it indicated that Leucine is more surface active than Colistin.

TABLE 5

Theoretical and measured surface compositions by XPS based on carbon atoms for the co-spray dried ColCipLeu formulations in the mass ratios (1-1-1)

| | % Surface Composition (Theoretical) | | | % Surface Composition (Measured) | | |
|---|---|---|---|---|---|---|
| Formulation | Colistin | Leucine | Ciprofloxacin | Colistin | Leucine | Ciprofloxacin |
| ColCipLeu (1:1:1) | 33 | 33 | 33 | 34 | 44 | 22 |

Figure 7C:
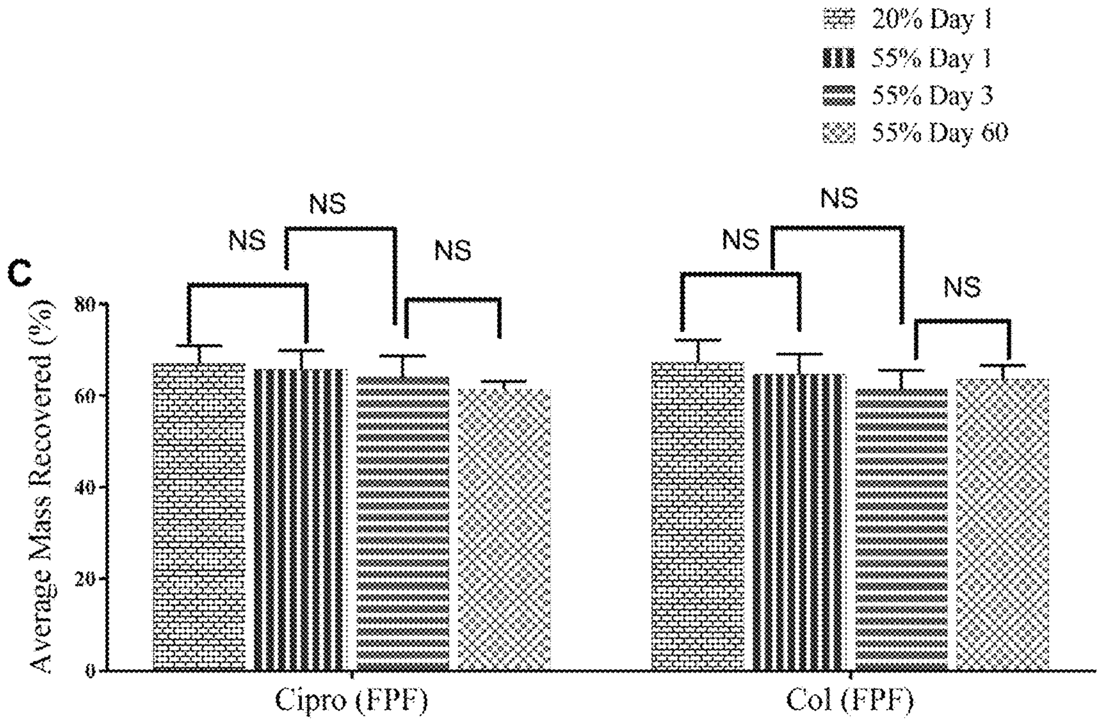

Particle engineering such as spray drying is being explored to produce particles of optimal morphologies and surface properties that provide optimum aerosol performance. However, many spray dried small molecules such as Ciprofloxacin are amorphous and tend to crystallize upon storage. Our earlier study showed the amorphous spray dried Ciprofloxacin crystallized at RH of 55% within one hour which led to an significant increase in FPF from 35.5±1.7% at Day 1 to 42.3±0.9% at Day 3 ($p<0.01$) (Shetty N. et al. *Pharm. Res.* 2018, 35, 7). Unlike Ciprofloxacin, amorphous form of the spray dried Colistin formulations can be retained in their amorphous form on storage at 60% RH and 25° C. for up to 3 months with no significant change in aerosol performance indicating the physical stability. In this study, we aimed to examine if the composite particles of Ciprofloxacin and Colistin have improved physical stability. Data showed the co-spray dried formulation of Ciprofloxacin with Colistin in a mass ratio of 1:1 remained amorphous for up to 60 days when stored at 55% RH (FIG. 1E). There was no change in the particle morphology and no significant change in aerosol performance ($p>0.05$), which indicated the physical and aerosolization stability (FIGS. 9 and 7C, respectively). Co-spray dried ColCipro formulation in the mass ratio (1:3) and (1:9) crystallized after 3 days of storage at 55% RH (FIG. 1D). Qualitatively degree of crystallization in these formulations appears to be lower as compared to spray dried Ciprofloxacin alone. However, no change in particle morphology and aerosol performance was observed in these formulations at 55% RH for up to 60 days. Based on the PXRD and SEM results we believe that during spray drying due to the large size of Colistin molecule compared to Ciprofloxacin it migrates to the surface of the co-spray dried formulation during rapid drying cycle. Our hypothesis is that Colistin is on the surface and thus crystallization at the surface is prevented. We propose the amorphous Colistin with larger molecular weight acts as a polymer-like matrix that minimizes the mobility and interactions between Ciprofloxacin-Ciprofloxacin and Ciprofloxacin-water molecules, therefore inhibits the crystallization tendency for amorphous Ciprofloxacin. Also, Colistin improves aerosol performance of Ciprofloxacin when co-spray dried (FIG. 8). There was an increase in aerosol performance of Ciprofloxacin by increasing Colistin concentrations from 10% to 50% w/w. The FPF of co-spray dried Colistin-Ciprofloxacin formulation even in the mass ratio (1:9) was significantly higher ($p<0.0001$) than that of spray dried Ciprofloxacin alone. We hypothesize that Colistin improved the aerosol performance by enriching on the particle surfaces, which was confirmed by XPS, Tof-SIMS and EDX. Our earlier studies showed Colistin has self-assembling and surface-active properties with a low surface energy; thus, surface enrichment of Colistin resulted in improved aerosolization.

The co-spray dried Ciprofloxacin-Colistin formulation (1:1) crystallized upon exposure to 75% RH for a day and subsequent increase in degree of crystallization was observed as stored at 75% RH from Day 1 to Day 7. Upon storage at 75% RH for 7 days the powders appeared to be fused with a significant decrease in FPF of ciprofloxacin from 71.5±1.7% at day 1 down to 19.2±1.4% at day 7. It has been observed that at high relative humidity conditions such as 75% RH, Colistin powders absorbed a significant amount of water, which led to substantial deterioration of aerosolization due to enhanced inter-particulate capillary forces. When the hygroscopic powders are stored at such humid environment for some time, water condensed on the particle surfaces may dissolve the surface component (i.e. Colistin) and form liquid bridges between particles. Such liquid bridges likely cause strong bonding between contacted particles and lead to poor aerosolization.

In order to overcome such negative effects of elevated humidity, leucine was added in the combination formulation. The amino acid, L-leucine, has been widely used to reduce cohesion and improve aerosolization of cohesive fine particles. Our studies showed that effects of L-leucine on aerosolization enhancement depend on whether L-leucine is enriched on the particle surfaces. Li et al. reported that enrichment of crystalline L-leucine on particle surface could provide protection against moisture on dispersion of hygroscopic powders (Li L, et al., *Eur. J. Pharm. Biopharm.* 2016, 102, 132-141). The data showed a slight crystallization of ciprofloxacin in the co-spray dried Colistin-Ciprofloxacin-leucine (ColCipLeu) formulation in the mass ratio (1:1:1) upon storage at 75% RH for 7 days; but there was no change in surface morphology of the co-spray dried formulation. XPS data revealed that L-leucine was enriched on the surface of the co-spray dried ColCipLeu (1:1:1) formulation, which contributed to the unchanged FPF when it was stored at 75% RH. Our study also indicated L-leucine is more surface-active than Colistin, leading to more L-leucine on the composite particle surface.

To summarize, we developed a combination DPI formulation of Ciprofloxacin and Colistin through co-spray drying. Colistin in the formulation inhibited the tendency of amorphous Ciprofloxacin to crystallize when stored at 55% RH, resulting in enhanced physical stability. Such inhibition effect could be due to polymer-like properties of Colistin that acts as a matrix material and reduces the molecular mobility of Ciprofloxacin. Moreover, addition of Colistin improved the aerosolization as compared to the spray dried Ciprofloxacin alone formulation, which is attributed to enrichment of Colistin on the surface of the co-spray dried formulation as measured by XPS, EDX and Tof-SIMS. Further addition of L-leucine even prevented moisture-induced deterioration in aerosolization as stored at 75% RH. Our study for the first time demonstrated that co-spray drying Ciprofloxacin with a synergistic antibiotic Colistin not only enhances the physical stability of amorphous dry powder formulation but also improves the aerosolization through surface enrichment of Colistin. The in-vivo synergistic efficacy of such combination formulation is examined using our established animal lung infections models (Lin Y W, et al., *Antimicro. Agents Chemother.* 2018, 62, e01790).

Those skilled in the art will recognize that numerous modifications can be made to the specific implementations described above. The implementations should not be limited to the particular limitations described. Other implementations may be possible.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected. It is intended that the scope of the present methods and apparatuses be defined by the following claims. However, it must be understood that this disclosure may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims.

What is claimed is:

1. A process for manufacturing a dry powder composition consisting of leucine, dual antibiotics of a polymycin and a quinolone, comprising the steps of a. dissolving leucine, a polymyxin compound and a quinolone compound, or a pharmaceutically acceptable salts thereof, respectively, in an aqueous or an organic medium to prepare a solution;

b. adding one or more pharmaceutically acceptable excipients to said solution; and c. spray-drying to afford said dry powder composition of dual antibiotics with an improved inhalable fraction of said antibiotics and an increased physical stability and aerosolization stability as compared with quinolone alone.

2. The process of claim 1, wherein said leucine comprises about 10% to 60% of the total solid weight.

3. The process of claim 1, wherein said polymyxin is colistin or a pharmaceutically acceptable salt thereof, and said quinolone is ciprofloxancin or a pharmaceutically acceptable salt thereof.

4. The process of claim 1, wherein said solution comprises about 5 to 200 mg of colistin and ciprofloxacin in a ratio of about 1:10 to about 10:1 (weight/weight) per milliliter.

5. The process of claim 1, wherein said aqueous medium is water or an aqueous solution of an organic solvent selected from the group consisting of acetonitrile, methanol, ethanol, or isopropyl alcohol wherein said organic solvent is to improve the solubility of drug material polymyxin and quinolone compounds which could not be fully dissolved in pure water.

6. A dry powder composition manufactured according to the process of claim 1, wherein said leucine comprises about 10% to 60% of the total solid weight of leucine, polymyxin and quinolone compounds mixture.

7. A pharmaceutical composition comprising a product manufactured according to the process of claim 1 together with one or more pharmaceutically acceptable excipients.

8. A pharmaceutical composition comprising a product manufactured according to the process of claim 2 together with one or more pharmaceutically acceptable excipients.

9. A pharmaceutical composition consisting of leucine and dual antibiotics of a polymycin and a quinolone manufactured according to a process of:

a. dissolving leucine, said polymycin and said quinolone, or pharmaceutically acceptable salts thereof, in an aqueous or an organic medium to prepare a solution;

b. adding one or more pharmaceutically acceptable excipients to said solution; and c. spray-drying to afford said pharmaceutical composition of dual antibiotics with an improved inhalable fraction of said antibiotics and an increased physical stability and aerosolization stability as compared with quinolone alone.

10. The pharmaceutical composition manufactured according to claim 9, wherein said leucine comprises about 10% to 60% of the total solid weight of leucine, said polymycin and said quinolone mixture.

11. The pharmaceutical composition manufactured according to claim 9, wherein said solution comprises about 5 to 200 mg of said polymycin and said quinolone per milliliter.

12. The pharmaceutical composition manufactured according to claim 11, wherein said polymycin and said quinolone are in a ratio of about 1:10 to about 10:1 (weight/weight).

13. The pharmaceutical composition manufactured according claim 9 is administered by inhalation.

14. A method for treating a patient with a bacterial infection comprising the step of administering a therapeutically effective amount of a pharmaceutical composition to a patient in need of relief from said infection, wherein said pharmaceutical composition consisting of leucine, a quinolone, and a polymycin is manufactured according to a process comprising the steps of a. dissolving said leucine, polymycin and quinolone antibiotics, or pharmaceutically acceptable salts thereof, in an aqueous or an organic medium to prepare a solution;

b. adding one or more pharmaceutically acceptable excipients to said solution; and c. spray-drying to afford said pharmaceutical composition of dual antibiotics of said polymycin and said quinolone with an improved inhalable fraction of said antibiotics and an increased physical stability and aerosolization stability as compared with quinolone alone.

15. The method according to claim 14, wherein said leucine comprises about 10% to 60% of the total solid weight of leucine, said polymycin and said quinolone mixture.

16. The method according to claim 14, wherein said polymycin is colistin or a pharmaceutically acceptable salt thereof, and said quinolone is ciprofloxancin or a pharmaceutically acceptable salt thereof.

17. The method according to claim 14, wherein said infection is an infection of the lungs.

18. The method according to claim 14, wherein said infection is caused by *Pseudomonas aeruginosa, Acinetobacter baumannii* and *Klebsiella pneumoniae.*

19. The method according to claim 14, wherein said pharmaceutical composition is administered by inhalation.

* * * * *